United States Patent
Galan et al.

(10) Patent No.: US 10,143,743 B2
(45) Date of Patent: Dec. 4, 2018

(54) NON-REPLICATING BACTERIAL NANOPARTICLE DELIVERY SYSTEM AND METHODS OF USE

(71) Applicant: Yale University, New Haven, CT (US)

(72) Inventors: Jorge Galan, New Haven, CT (US); Heather Carleton, Decatur, GA (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 14/529,424

(22) Filed: Oct. 31, 2014

(65) Prior Publication Data
US 2015/0140037 A1 May 21, 2015

Related U.S. Application Data

(60) Provisional application No. 61/905,602, filed on Nov. 18, 2013.

(51) Int. Cl.
*A61K 39/39* (2006.01)
*A61K 39/00* (2006.01)

(52) U.S. Cl.
CPC .... *A61K 39/39* (2013.01); *A61K 2039/55522* (2013.01); *A61K 2039/55555* (2013.01); *A61K 2039/55594* (2013.01)

(58) Field of Classification Search
CPC .................................................. A61K 39/39
See application file for complete search history.

(56) References Cited

U.S. PATENT DOCUMENTS

| | | | | |
|---|---|---|---|---|
| 2006/0068469 A1* | 3/2006 | Payne | ................ | A61K 48/0008 435/69.1 |
| 2012/0207754 A1* | 8/2012 | Giacalone | ............ | C07K 14/195 424/134.1 |
| 2015/0238590 A1* | 8/2015 | Picking | .............. | A61K 39/0275 424/190.1 |

OTHER PUBLICATIONS

Carleton et al., Nature Communications 4:1590 , 2013.*
Russmann et al., 1998, Delivery of Epitopes by the *Salmonella* Type III Secretion System for Vaccine Development, Science, 281: 565-568.
Chen et al., 2006, Optimization of the Delivery of Heterologous Proteins by the *Salmonella enterica* Serovar Typhimurium Type III Secretion System for Vaccine Development, Infect Immun, 74: 5826-5833.
Giacalone et al., 2006, Immune responses elicited by bacterial minicells capable of simultaneous DNA and protein antigen delivery, Vaccine 24:6009-6017.
Palm and Medzhitov, 2009, Pattern recognition receptors and control of adaptive immunity, Immunol Rev. 227:221-233.
Patel et al., 2009, Diversification of a *Salmonella* Virulence Protein Function by Ubiquitin-Dependent Differential Localization, Cell 137:283-294.
Collazo and Galán, 1997, The invasion-associated type III system of *Salmonella typhimurium* directs the translocation of Sip proteins into the host cell, Mol. Microbiol. 24:747-756.
Lara-Tejero and Galan, 2009, *Salmonella enterica* Serovar Typhimurium Pathogenicity Island 1-Encoded Type III Secretion System Translocases Mediate Intimate Attachment to Nonphagocytic Cells, Infect Immun 77:2635-2642.
Galyov et al., 1997, A secreted effector protein of *Salmonella* dublin is translocated into eukaryotic cells and mediates inflammation and fluid secretion in infected ileal mucosa, Mol Microbiol 25:903-912.
Zierler and Galan, 1995, Contact with cultured epithelial cells stimulates secretion of *Salmonella typhimurium* invasion protein InvJ., Infect Immun 63:4024-4028.
Kubori et al., 1998, Supramolecular Structure of the *Salmonella typhimurium* Type III Protein Secretion System, Science 280:602-605.
Evans et al., 2003, Mucosal Priming of Simian Immunodeficiency Virus-Specific Cytotoxic T-Lymphocyte Responses in Rhesus Macaques by the *Salmonella* Type III Secretion Antigen Delivery System, J. Virol. 77:2400-2409.
Galan and Wolf-Watz, 2006, Protein delivery into eukaryotic cells by type III secretion machines, Nature 444:567-573.
Bajaj et al., 1996, Co-ordinate regulation of *Salmonella typhimurium* invasion genes by environmental and regulatory factors is mediated by control of hilA expression, Mol. Microbiol. 22(4):703-714.
Frazer and Curtiss, 1975, Production, properties and utility of bacterial minicells, Curr Top Microbiol Immunol. 69:1-84.

* cited by examiner

*Primary Examiner* — Jana A Hines
*Assistant Examiner* — Khatol S Shahnan Shah
(74) *Attorney, Agent, or Firm* — Riverside Law LLP

(57) ABSTRACT

The present invention provides compositions and methods for the secretion and the translocation of a compound of interest by a bacterial minicell. In certain embodiments, the invention provides a bacterial minicell comprising at least one component of the type III secretion system (T3SS), which provides a safe and efficient system for secretion and translocation. In one embodiment, the invention allows for the delivery of an antigen to a cell or subject in order to induce an immune response.

9 Claims, 10 Drawing Sheets

Specification includes a Sequence Listing.

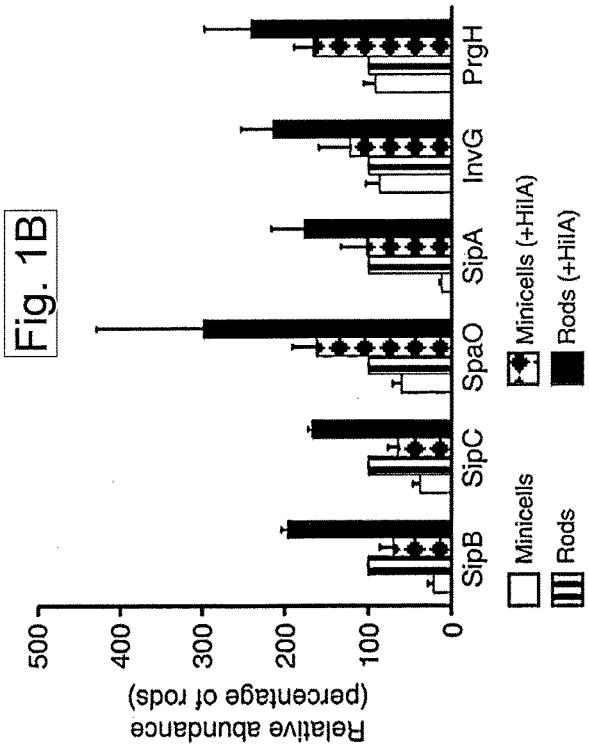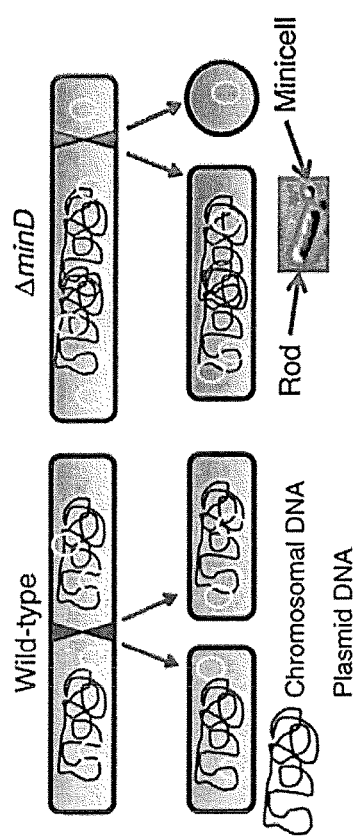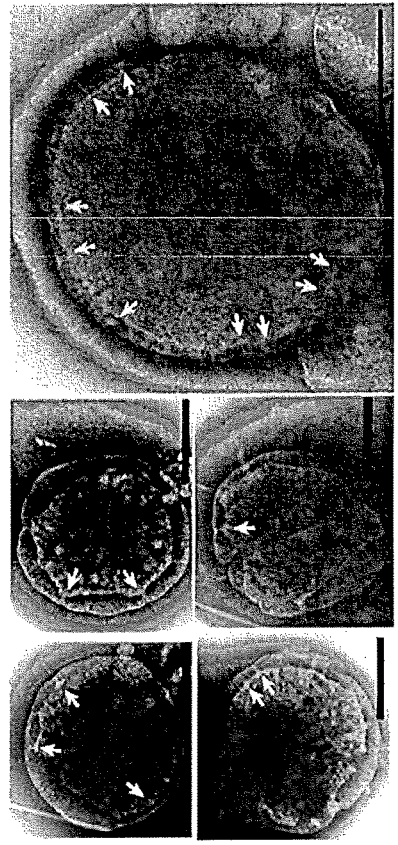

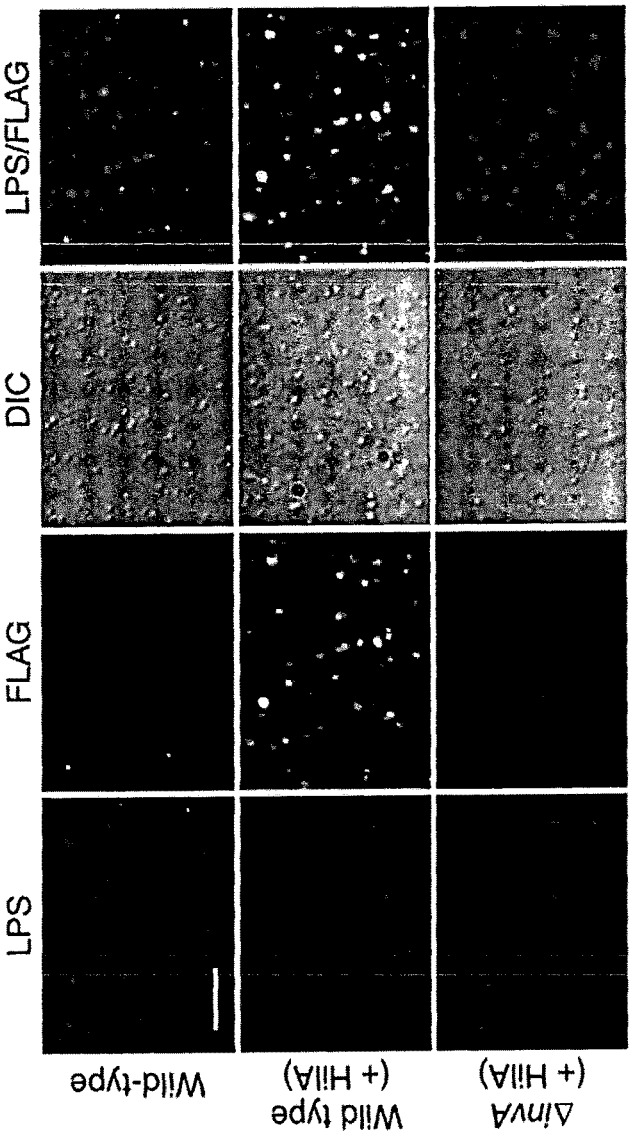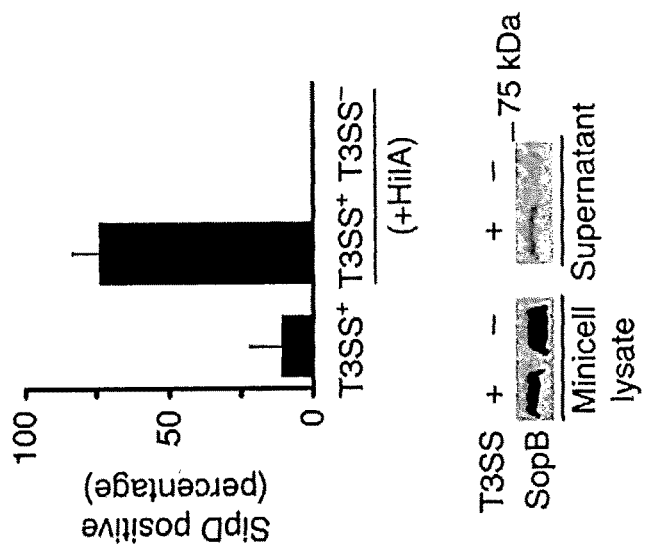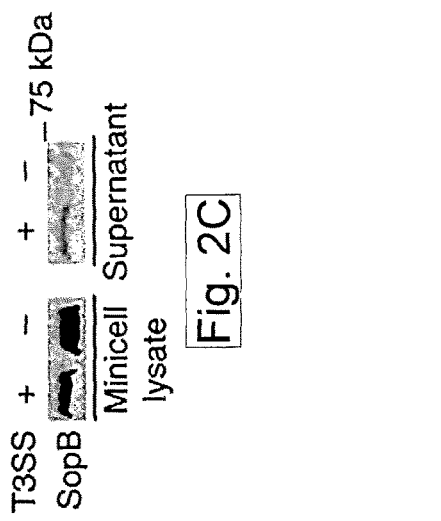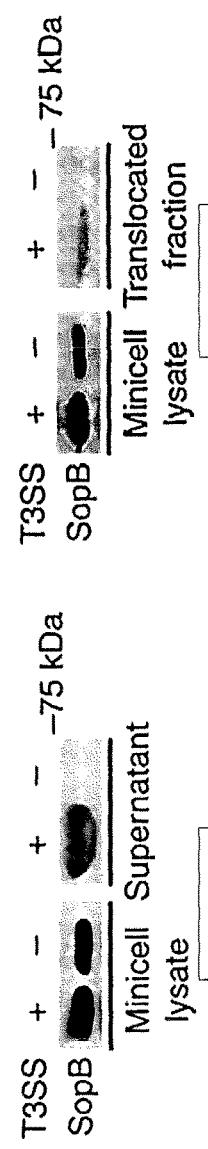

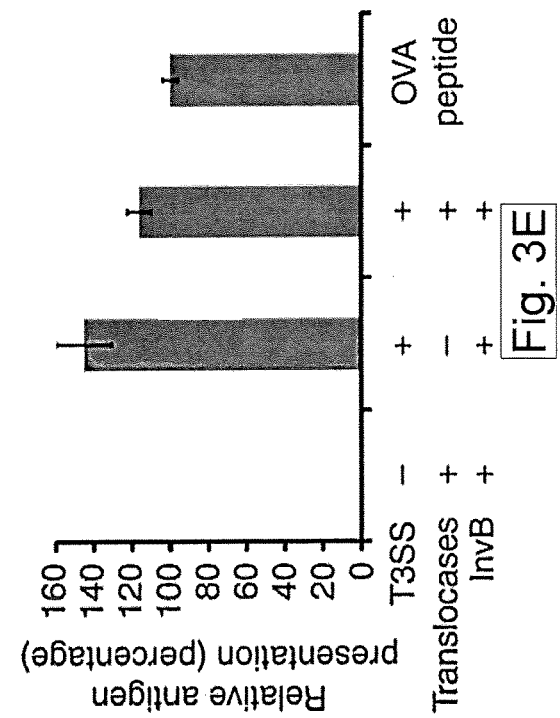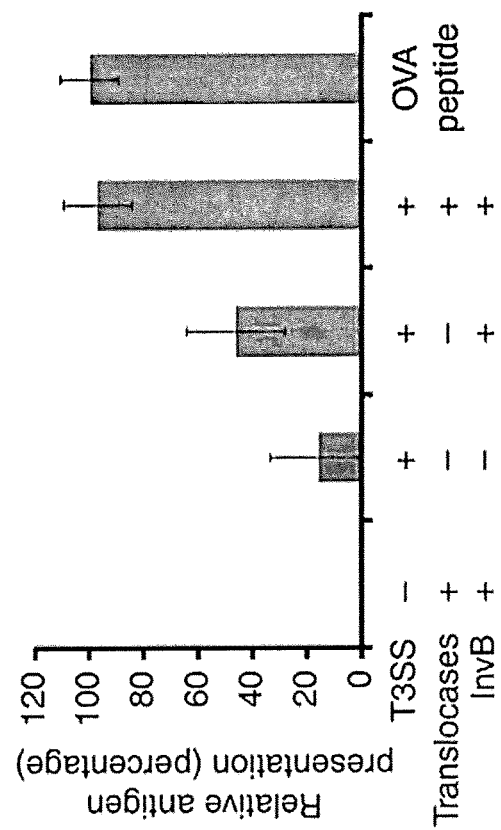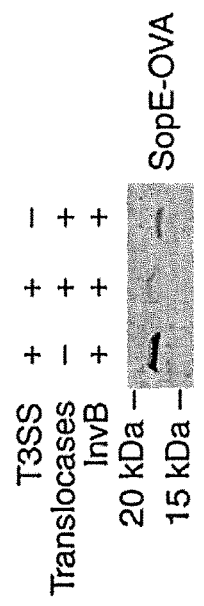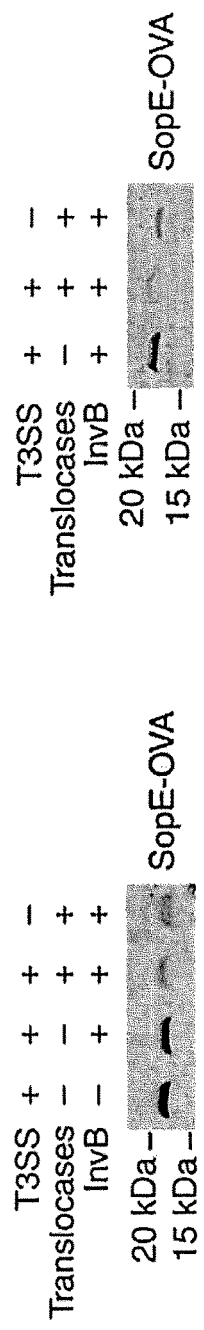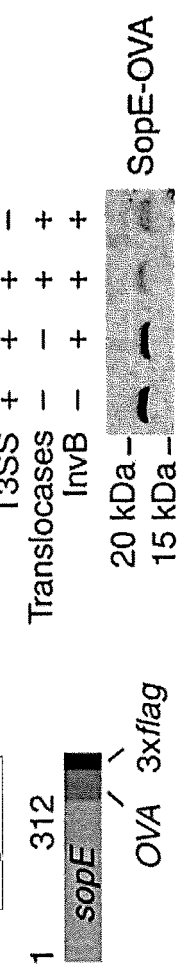

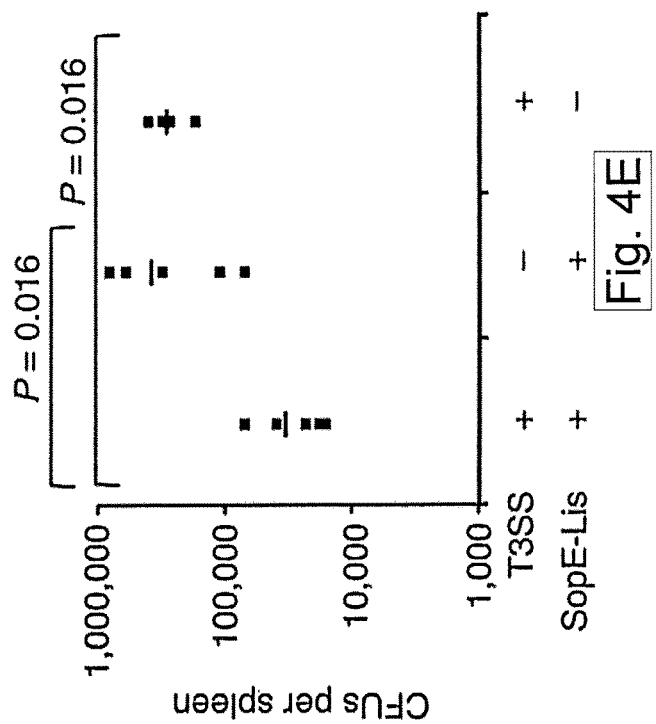
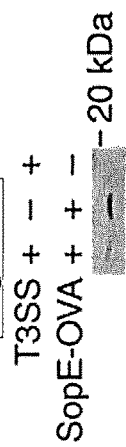
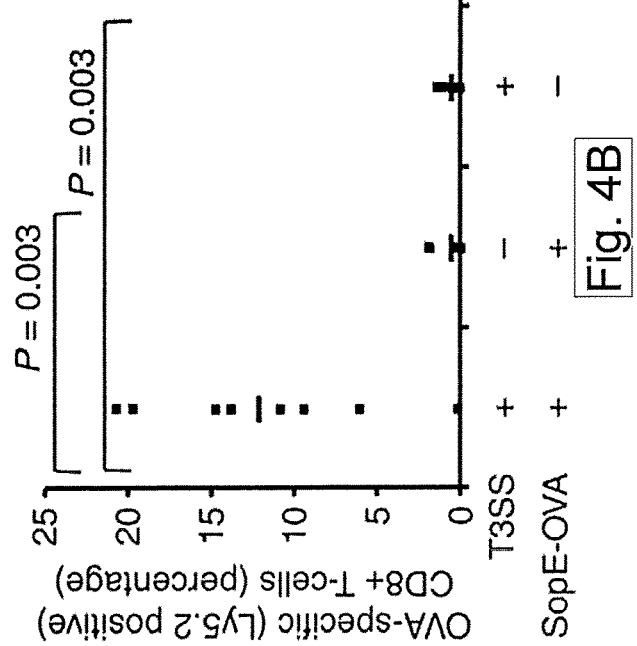

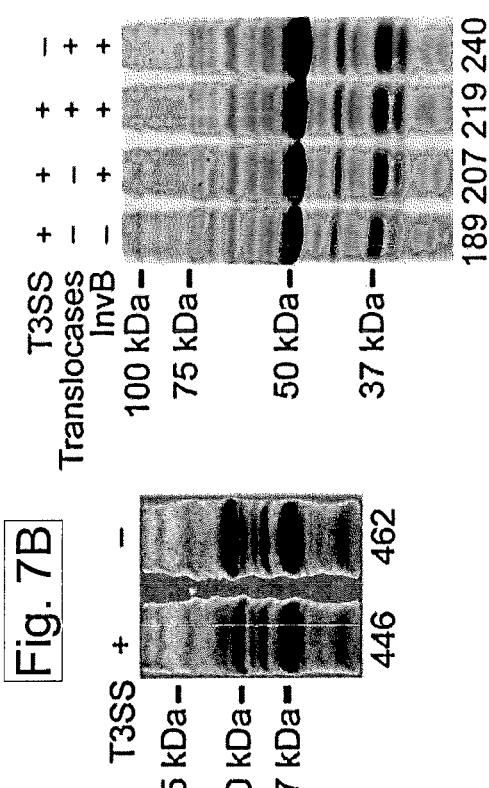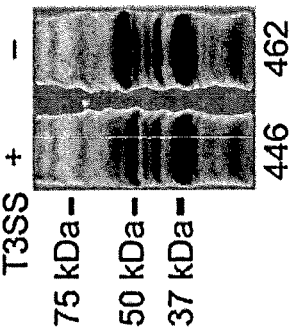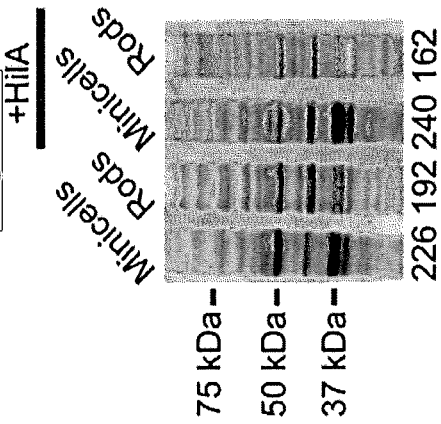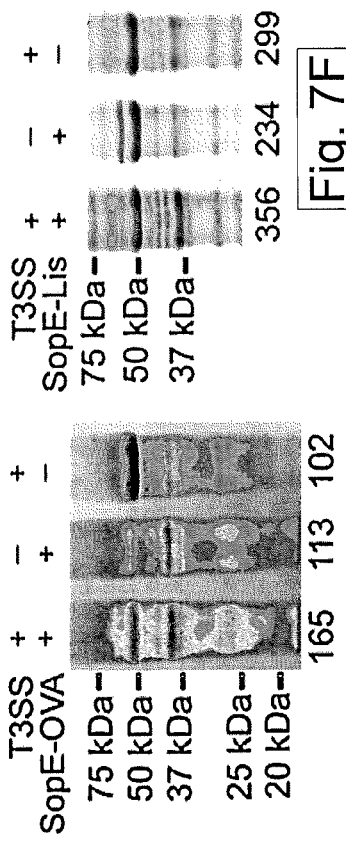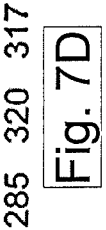
Fig. 7A Fig. 7B Fig. 7C Fig. 7D Fig. 7E Fig. 7F

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Chemically synthesized

<400> SEQUENCE: 1

Ser Ile Ile Asn Phe Glu Lys Leu
1               5

NON-REPLICATING BACTERIAL NANOPARTICLE DELIVERY SYSTEM AND METHODS OF USE

CROSS-REFERENCE TO RELATED APPLICATIONS

This application claims priority to U.S. Provisional Patent Application No. 61/905,602 filed Nov. 18, 2013, the contents of which are incorporated by reference herein in their entirety.

STATEMENT REGARDING FEDERALLY SPONSORED RESEARCH OR DEVELOPMENT

This invention was made with government support under Grant No. AI030492, awarded by the NIH National Institute of Allergy and Infectious Diseases. The government has certain rights in the invention.

BACKGROUND OF THE INVENTION

Efficient vaccines must not only stimulate innate immune receptors, but also deliver antigens to specific subcellular compartments so that they can be processed via the class I and class II antigen-presenting pathways and lead to the production of antigen-specific cytotoxic T cells and antibodies (Amanna and Slifka, 2011, Virology 411:206-215). Live replicating pathogenic bacteria, such as *Salmonella typhimurium*, rendered avirulent and engineered with the ability to express foreign antigens are being considered as vaccine vectors to protect against various infectious diseases or as therapeutic agents against cancer (Curtiss et al., 2010, Crit Rev Immunol. 30:255-270; Hegazy and Hensel, 2012, Future Microbiol. 7:111-127; Moreno, et al., 2010, Curr Gene Ther. 10(1):56-76). Although they potently stimulate innate immune receptors, one limitation of these bacterial vaccine systems is their inefficient capacity to stimulate cytotoxic T cell responses (Gao et al., 1992, Infect. Immun. 60:3780-3789; Yang et al., 1990, J. Immunol. 145:2281-2285), which require the delivery of antigens to the cytosol of antigen presenting cells. This limitation has been largely overcome by the use of type III secretion systems (T3SS) (Chen et al., 2006, Infect Immun 74:5826-5833; Russmann et al., 1998, Science 281:565-568), which are complex multi-protein molecular machines that deliver bacterial virulence effector proteins into the host cell cytosol (Galan and Wolf-Watz, 2006, Nature 444:567-573). Proteins destined to travel the T3SS pathway possess discrete signals that direct them to the secretion machine (Arnold et al., 2010, Microbes Infect. 12:346-358). When incorporated into heterologous proteins, these signals can target virtually any protein for delivery through this secretion pathway (Chen et al., 2006, Infect Immun 74:5826-5833; Michiels and Cornelis, 1991, J. Bacteriol. 173:1677-1685). Consequently, T3SS have been engineered to deliver heterologous antigens in the context of virulence attenuated bacterial pathogens (Russmann et al., 1998, Science 281:565-568). Heterologous protein antigens delivered by this system have been shown to stimulate antigen specific $CD8^+$ T-cells, which in animal models conferred protection to a variety of infectious diseases or caused the regression of established tumors (Russmann et al., 1998, Science 281:565-568; Russmann et al., 2001, J Immunol 167:357-365; Wieser et al., 2012, Int J Med Microbiol. 302:10-18; Zhu et al., 2010, Cancer Science 101:2621-2628; Chamekh, 2010, Immunopharmacol Immunotoxicol. 32:1-4; Tartz et al., 2008, Vaccine 26:5935-5943; Nishikawa et al., 2006, J. Clin. Inv. 116:1946-1954; Konjufca et al., 2006, Infection and Immunity 74:6785-6796; Evans et al., 2003, J. Virol. 77:2400-2409; Kotton et al., 2006, Vaccine 24:6216-6224; Sevil et al., 2008, Vaccine 26:1879-1886). A second limitation of the virulence-attenuated bacterial vaccine systems relates to their safety. Residual virulence of the attenuated pathogen or the potential for virulence-reversion may limit their use in certain populations such as children or the immunocompromised.

Since protein translocation by T3SSs requires energy provided by ATP hydrolysis and a proton gradient (Galán, 2008, Nat Struct Mol Biol. 15:127-128), the use of this system has been restricted to the context of live virulence-attenuated bacteria. The intrinsic complexity of the assembly of this large, multi-protein machine combined with its energy requirements, preclude the development of a synthetic system capable of supporting the function of T3SS.

Therefore, there is a need in the art for compositions and methods for an efficient non-replicating antigen-delivery system that can be used for vaccines and immunotherapy. The present invention satisfies this unmet need.

SUMMARY OF THE INVENTION

In one aspect, the present invention provides a composition comprising a bacterial minicell comprising the components of the type III secretion system (T3SS) and a compound of interest, wherein the bacterial minicell secretes the compound of interest. In one embodiment, the bacterial minicell is derived from bacteria. In one embodiment, the bacteria is replication deficient and capable of generating minicells. In one embodiment, the bacteria comprises a mutant form of at least one selected from the group consisting of minA, minB, minC, minD, ftsA, ftsZ, and zipA, thereby rendering the bacteria replication deficient.

In one embodiment, the bacterial minicell is modified to increase the expression of at least one selected from the group consisting of a T3SS component and a T3SS regulator. In one embodiment, the bacterial minicell comprises at least one isolated nucleic acid comprising a nucleic acid sequence encoding at least one of the group consisting of HilA, InvB, SipB, SipC, SipD, InvE, SicA, and SigE.

In one embodiment the compound of interest is an antigen. In one embodiment, the compound of interest is selected from the group consisting of a peptide, a protein, a nucleic acid, and a small molecule.

In one embodiment, the composition is a vaccine delivery system.

In one aspect, the present invention provides a method of delivering a compound of interest into a recipient cell. The method comprises contacting the recipient cell with the compound of interest, wherein the compound of interest was secreted by a bacterial minicell, thereby delivering the compound of interest to the recipient cell, wherein the bacterial minicell comprises a functional type III secretion system (T3SS) and the compound of interest. In one embodiment, the bacterial minicell is derived from bacteria. In one embodiment, the bacteria is replication deficient and capable of generating minicells. In one embodiment, the bacteria comprises a mutant form of at least one selected from the group consisting of minA, minB, minC, minD, ftsA, ftsZ, and zipA, thereby rendering the bacteria replication deficient.

In one embodiment, the bacterial minicell is modified to increase the expression of at least one selected from the group consisting of a T3SS component and a T3SS regulator. In one embodiment, the bacterial minicell comprises at least one isolated nucleic acid comprising a nucleic acid sequence encoding at least one of the group consisting of HilA, InvB, SipB, SipC, SipD, InvE, SicA, and SigE.

In one embodiment the compound of interest is an antigen. In one embodiment, the recipient cell is an antigen presenting cell. In one embodiment, the compound of interest is selected from the group consisting of a peptide, a protein, a nucleic acid, and a small molecule.

In one embodiment, the bacterial minicell and recipient cell are in an environment selected from in vivo, ex vivo, or in vitro.

In one aspect, the present invention provides a method of inducing an immune response comprising contacting an antigen presenting cell to an antigen secreted by a bacterial minicell, thereby delivering the antigen to the antigen presenting cell, wherein the bacterial minicell comprises one or more components of the type III secretion system (T3SS). In one embodiment, the bacterial minicell is derived from bacteria. In one embodiment, the bacteria is replication deficient and capable of generating minicells. In one embodiment, the bacteria comprises a mutant form of at least one selected from the group consisting of minA, minB, minC, minD, ftsA, ftsZ, and zipA, thereby rendering the bacteria replication deficient.

In one embodiment, the bacterial minicell is modified to increase the expression of at least one selected from the group consisting of a T3SS component and a T3SS regulator. In one embodiment, the bacterial minicell comprises at least one isolated nucleic acid comprising a nucleic acid sequence encoding at least one of the group consisting of HilA, InvB, SipB, SipC, SipD, InvE, SicA, and SigE.

In one embodiment, the bacterial minicell and antigen presenting cell are in an environment selected from the group consisting of in vivo, ex vivo, or in vitro.

In one embodiment, the antigen presenting cell is administered to a subject in need thereof. In one embodiment, the method comprises contacting the antigen presenting cell to a T cell, thereby activating the T cell.

In one embodiment, the method treats or prevents a disorder associated with the antigen in a subject in need. In one embodiment, the disorder is selected from the group consisting of cancer and infectious disease.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A through FIG. 1D, depicts the results of experiments demonstrating that bacterial minicells assemble a type III secretion system. (FIG. 1A) Schematic of minicell generation (see also FIG. 5). (FIG. 1B) Relative abundance of selected T3SS proteins analyzed by immunoblotting. Values are standardized compared to those obtained from wild-type S. typhimurium rods and normalized according to the total protein concentration of each sample. Values are the mean±standard deviation of 3 independent measurements. (FIG. 1C) Electron micrographs of negatively-stained osmotically-shocked minicells. Arrows indicate T3SS needle complexes on the minicell envelope. Scale bars: 200 nm. (FIG. 1D) Electron micrographs of negatively-stained needle complexes isolated from purified minicells. Scale bars: 100 nm (top) and 50 nm (bottom).

FIG. 2, comprising FIG. 2A through FIG. 2E, depict the results of experiments demonstrating that the type III secretion system in minicells is functional. (FIG. 2A and FIG. 2B) Detection of the needle complex tip protein SipD on the surface of purified minicells. Minicells were isolated from wild-type or T3SS-defective (ΔinvA) S. typhimurium strains expressing SipD-FLAG and carrying a plasmid expressing the SPI-1 T3SS positive transcriptional regulator HilA. Minicells were stained with an antibody to LPS, an antibody against the FLAG tag, and examined by immunofluorescence and DIC microscopy. Scale bar: 2.5 µm (FIG. 2A). The % of minicells showing surface SipD stain is shown (FIG. 2B). Values represent the mean±standard deviation of three independent experiments in which a minimum of 4,000 cells per strain were counted. (FIG. 2C and FIG. 2D) Secretion of de novo synthesized effector proteins by purified minicells through their SPI-1 T3SS. Minicells were isolated from wild type or T3SS-defective (ΔinvA) S. typhimurium strains carrying a plasmid encoding the SPI-1 T3SS effector SopB expressed under the control of an arabinose-inducible promoter. Isolated minicells were incubated for 3 hrs in the presence of arabinose and the presence of SopB in minicell lysates and supernatants were analyzed by western blot (FIG. 2C). Alternatively, minicells were exposed to cultured Henle-407 cells and the presence of SopB in supernatants examined as described above (FIG. 2D). (FIG. 2E) Minicell-mediated, type III secretion dependent protein translocation into cultured epithelial cells. Henle-407 cells were treated with minicells isolated from type III secretion competent or type III secretion-defective (ΔinvA) as described above and added to Henle-407 cells for 2.5 hs. The presence of the effector protein SopB in minicell lysates and the translocated fraction was assayed by Western blot.

FIG. 3, comprising FIG. 3A through FIG. 3E, depicts the results of experiments demonstrating the T3SS-dependent antigen delivery by minicells in-vitro (FIG. 3A) Schematic of the SopE-OVA construct used in these studies. (FIG. 3B) Western blot analysis of minicells obtained from wild type or T3SS-defective (ΔinvA) S. typhimurium strains expressing the SopE-OVA construct and used in the experiment shown in (FIG. 3C). When indicated, the SopE-OVA construct was co-expressed with the SopE chaperone InvB and the T3SS protein translocases and their chaperones to improve protein secretion and/or translocation. Equal amount of total protein was loaded in each sample. (FIG. 3C) Analysis of antigen delivery by minicells to antigen-presenting cells. RMA cells (C57BL/6 mouse hybridomas) were pulsed for 3 hs with minicells isolated from wild type or T3SS-defective (ΔinvA) S. typhimurium strains. After pulsing, RMA cells were fixed, and used as APCs in a B3Z T-cell activation assay as described in experimental procedures. Values represent the levels of antigen presentation based on the β-galactosidase activity detected in the B3Z-T cell hybridoma reporter and are normalized relative to the values of the OVA peptide positive control, which was considered 100%. The values are the mean±standard deviation of three independent experiments. (FIG. 3D and FIG. 3E) Minicells can deliver antigen to dendritic cells ex vivo. (FIG. 3E) Western blot analysis of minicells obtained from wild type or T3SS-defective (ΔinvA) S. typhimurium strains expressing the SopE-OVA construct and used in the experiment shown in (FIG. 3E). Equal amount of total protein was loaded in each sample. (FIG. 3E) Bone marrow-derived dendritic cells were pulsed for 3 hs with minicells isolated from the indicated S. typhimurium strains carrying a plasmid expressing SopE-OVA and the indicated SPI-1 T3SS-associated proteins. After pulsing, dendritic cells were fixed and used as APCs in a B3Z T-cell activation assay. Values represent the levels of antigen presentation based on the β-galactosidase activity detected in the B3Z-T cell hybridoma reporter and they are normalized relative to the values of the OVA peptide positive control, which was considered 100%. The values are the mean±standard deviation of three independent experiments.

FIG. 4, comprising FIG. 4A through FIG. 4E, depicts the results of experiments demonstrating the T3SS-dependent priming of protective CD8+ T-cell responses by minicells. (FIG. 4A) Western blot analysis of minicells obtained from wild type or T3SS-defective (ΔinvA) S. typhimurium strains expressing the SopE-OVA construct and used in the experiment shown in (FIG. 4B). Equal amount of total protein was loaded in each sample. (FIG. 4B) Splenocytes from OT-I mice were adoptively transferred into recipient mice (C57BL/6/CD45.1), which were subsequently immunized with minicells isolated from the indicated S. Typhimurium Δasd strains expressing SopE-OVA. Three weeks after minicell immunization, mice were boosted and the levels of OVA-specific CD8+ T cells were measured by flow cytometry. Values represent the percentage of OVA-specific CD8+ T-cells in each individual mouse (number of mice used in each category: T3SS+/SopE-OVA+:9; T3SS−/SopE-OVA+: 7; T3SS+/SopE-OVA−:7; transfer alone: 4) (FIG. 4C) Schematic of SopE-Lis construct used in the protection experiments. (FIG. 4D) Western blot analysis of minicells obtained from wild type or T3SS-defective (ΔinvA) S. typhimurium strains expressing the SopE-Lis construct and used in the experiment shown in FIG. 4E. (FIG. 4E) BMDCs prepared from Balb/c mice were incubated with minicells isolated from the indicated bacterial strains and transferred by tail vein injection into a Balb/c mouse. Six days after transfer, mice were challenged with L. monocytogenes, and 3 days after challenge the c. f. u. in spleens were determined (number of mice used in each category: T3SS+/SopE-Lys+: 5; T3SS−/SopE-Lys+: 5; T3SS+/SopE-Lys−: 4).

FIG. 7, comprising FIG. 7A through FIG. 7F, depicts the results of experiments used to determine protein content used to standardized loading in the Western blot analyses of the different samples utilized in the studies described herein. Lysates from the indicated samples were separated by SDS-PAGE, stained with Coomassie blue, and the gels scanned on an Odyssey infrared imaging system (LI-COR Biosciences). Values below each lane correspond to the integrated intensity of the entire lane. Samples in FIG. 7A correspond to experiments shown in FIG. 1C, samples in FIG. 7B correspond to experiments shown in FIG. 2C, samples in FIG. 7C correspond to experiments shown in FIG. 3B, samples in FIG. 7D correspond to experiments shown in FIG. 3D, samples in FIG. 7E correspond to experiments shown in FIG. 4A, and samples in FIG. 7F correspond to experiments shown in FIG. 4D.

DETAILED DESCRIPTION

Figure 5:
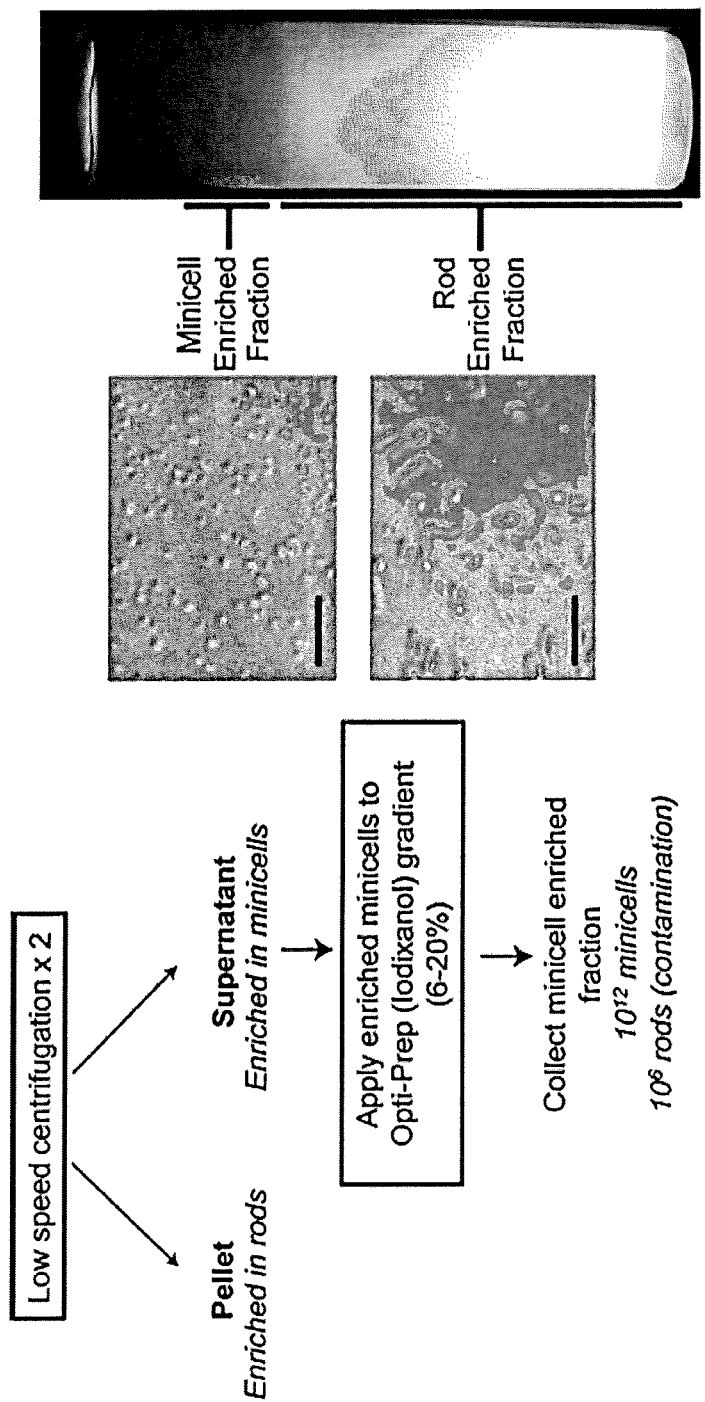
FIG. 5 depicts a diagram of an exemplary minicell isolation protocol. DIC images obtained from the indicated fractions of a 5-20% iodixanol gradient are shown. Scale bar: 2 µm.

The present invention provides compositions and methods for the delivery of a compound of interest. The invention is based upon the discovery of nanoparticles derived from replication-deficient bacteria (i.e. bacterial minicells), which retain the ability to secrete and deliver a desired compound via the type III secretion system (T3SS). In one embodiment, the present invention provides a bacterial minicell which comprises a functional T3SS. In certain embodiments, the bacterial minicell of the invention is used as a vaccine delivery system to deliver a desired antigen to a recipient cell, such as an antigen presenting cell (APC). The present invention provides for a safe and efficient delivery system that, in certain instances, is used for vaccination and cellular immunotherapy.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular activity, such as proliferation, cytokine production, or detectable effector functions. The term "activated T cells" refers to, among other things, T cells that are undergoing cell division.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

An "antigen presenting cell" (APC) is a cell that is capable of activating T cells, and includes, but is not limited to, monocytes/macrophages, B cells and dendritic cells (DCs).

The term "dendritic cell" or "DC" refers to any member of a diverse population of morphologically similar cell types found in lymphoid or non-lymphoid tissues. These cells are characterized by their distinctive morphology, high levels of surface MHC-class II expression. DCs can be isolated from a number of tissue sources. DCs have a high capacity for sensitizing MHC-restricted T cells and are very effective at presenting antigens to T cells in situ. The antigens may be self-antigens that are expressed during T cell development and tolerance, and foreign antigens that are present during normal immune processes.

The term "mature DC" as used herein, is defined as a dendritic cell that expresses high levels of MHC class II, CD80 (B7.1) and CD86 (B7.2) molecules. In contrast, immature dendritic cells express low levels of MHC class II, CD80 (B7.1) and CD86 (B7.2) molecules but have a great capacity to take up an antigen.

"Antigen-loaded APC" or an "antigen-pulsed APC" includes an APC, which has been exposed to an antigen and activated by the antigen. For example, an APC may become antigen-loaded by delivery of the antigen via a bacterial minicell which comprises the antigen.

As used herein, the term "autologous" is meant to refer to any material derived from the same individual to which it is later to be re-introduced.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods for the delivery of any compound of interest. For example, in certain embodiments, the invention provides a composition which secretes a compound contained therein. In one embodiment, the composition delivers the compound into a cell. For example, in one embodiment, the present invention provides for efficient antigen delivery which can be used for vaccine development and immunotherapy.

The present invention is based on the development of a non-replicating nanoparticle having the ability to deliver a compound of interest. In one embodiment, the nanoparticle is derived from a bacterial minicell. A minicell is an achromosomal particle formed from replication-deficient bacteria. The minicell is not a live, replicating bacterium, and therefore can be safely administered to a cell or to a subject, without the fear of infection. It is demonstrated herein that the minicell comprises the type III secretion system (T3SS), thereby allowing the minicell to efficiently deliver a compound of interest. Further, the minicell of the invention is shown to be able to translate isolated nucleic acid sequences, thereby allowing for the genetic modification of a minicell using standard techniques.

In one embodiment, the composition of the invention comprises a bacterial cell which produces a non-replicating bacterial minicell comprising one or more T3SS components. The present invention is not limited to any particular bacterial cell or any particular bacterial strain. In one embodiment, the bacterial cell is of the *Salmonella typhimurium* (*S. typhimurium*) strain.

In one embodiment, the composition comprises a genetically modified bacterial cell which produces a non-replicating minicell comprising one or more T3SS components. For example, in one embodiment, the bacterial cell is genetically modified to render the cell replication deficient. For example, in one embodiment, the bacterial cell is genetically modified to comprise a mutation which renders the cell replication deficient. For example, the cell may be modified to comprise in mutation in genes including, but not limited to, minA, minB, minC, minD, ftsA, ftsZ, and zipA. In one embodiment, the cell is modified to comprise a minD mutant allele. In certain instances, the modified cell expresses a mutated form of minD, which renders the cell replication deficient. In one embodiment, the bacterial cell is genetically modified to increase the expression of one or more T3SS components. For example, in one embodiment, the bacterial cell is genetically modified to increase the expression of InvB, SipB, SipC, SipD, InvE, SicA, SigE, or combinations thereof.

In one embodiment, the composition comprises a bacterial cell modified to express a compound of interest to be secreted through the T3SS system. The present invention is not limited to any particular compound. Rather, the present invention encompasses a cell modified to express and secrete any compound of interest. Exemplary compounds include, but are not limited to, peptides, proteins, nucleic acids, small molecules, and the like. For example, in one embodiment, the compound is an antigen which can be secreted or delivered to an antigen-presenting cell. In certain embodiments, the compound of interest is a chimera, wherein the chimera comprises a targeting domain which targets the chimera to the T3SS. In certain embodiments, the targeting domain is derived from proteins that are known to be delivered by T3SS, including but not limited to SopE, SptB, SopB, and SipA.

In one embodiment, the composition comprises a bacterial minicell derived from a replication-deficient bacterial strain. In one embodiment, the minicell comprises one or more T3SS components, thereby allowing the minicell to deliver a compound of interest. In one embodiment, the bacterial strain is modified to make the strain replication deficient, to increase the expression of one or more T3SS components, to express the compound of interest, or a combination thereof. The one or more T3SS components include, but are not limited to, InvB, SipB, SipC, SipD, InvE, SicA, and SigE, as well as other components listed herein in Table 4, Table 5, or Table 6. In certain embodiments, a minicell derived from a genetically modified bacterial cell comprises at least one isolated nucleic acid comprising a nucleic acid sequence encoding at least one T3SS regulator, T3SS component, or compound of interest to be secreted. An exemplary T3SS regulator, includes, but is not limited to, HilA.

In one embodiment, the invention provides a vaccine delivery system, comprising a bacterial minicell derived from a replication-deficient bacterial strain. In one embodiment, the minicell comprises one or more T3SS components, thereby allowing the minicell to deliver a compound of interest. In one embodiment, the bacterial strain is modified to make the strain replication deficient, to increase the expression of one or more T3SS components, to express the compound of interest, or a combination thereof. As described herein, the vaccine delivery system provides efficient antigen delivery, using a non-replicating bacterial minicell. The system thereby provides safe antigen delivery as the minicell is not a live bacteria.

In one embodiment, the invention provides a vaccine. In one embodiment, the vaccine comprises a bacterial minicell, as described herein. In one embodiment, the vaccine comprises an antigen presenting cell comprising a minicell-delivered antigen. In one embodiment, the vaccine comprises an activated T cell, activated via an antigen presenting cell comprising a minicell-derived antigen. In certain embodiments, the vaccine comprises a cellular component (e.g., antigen presenting cell, T cell, etc.) that was modified ex vivo. For example, in certain embodiments, the vaccine comprises an antigen presenting cell or T cell that was isolated from a subject to be vaccinated. In one embodiment, the antigen presenting cell is modified ex vivo to comprise a desired antigen, as delivered by the minicell of the invention.

In one embodiment, the present invention provides a method of delivering a compound to a recipient cell. For example, in one embodiment, the method comprises contacting the recipient cell with a compound secreted by a bacterial minicell. In one embodiment, the bacterial minicell is modified to express the compound. In certain embodiments, the recipient cell is contacted directly to the bacterial minicell to facilitate delivery of the compound from the minicell into the recipient cell. As described herein, the bacterial minicell of the invention comprises the T3SS thereby allowing safe and efficient delivery of any compound of interest. For example, in certain embodiments, the method provides direct delivery of the compound of interest into a eukaryotic cell, including for example an APC. That is, in one embodiment, the bacterial minicell of the invention injects the compound of interest into a recipient cell. In another embodiment, the bacterial minicell of the invention secretes the compound of interest into an extracellular space surrounding the recipient cell.

The present invention provides a method of stimulating an immune response in a subject. For example, in one embodiment, the method comprises delivering an antigen to an APC, by way of the T3SS of a bacterial minicell. The present invention is partly based upon the discovery that a bacterial minicell has the ability to secrete a desired antigen, and in certain instances deliver the antigen into a cell in order to stimulate an immune response. In one embodiment, the method allows for the delivery of the antigen to the class I antigen presenting pathway. In one embodiment, the method allows for simulating an MHC class I immune response. In certain embodiments, the method is used as a prophylactic or a therapeutic method.

In one embodiment, the method is used in cellular immunotherapy. For example, in one embodiment, autologous APCs are isolated from the subject and contacted ex vivo with one or more antigens secreted by one or more bacterial minicells. In one embodiment, the bacterial minicells express, secrete, and deliver an antigen to the APCs. In one embodiment, the APCs are then administered to the subject, which induces an immune response against the antigen. In one embodiment, the method comprises contacting the APCs with autologous T cells ex vivo, thereby activating the T cells. In one embodiment, the activated T cells are then administered to the subject. In certain embodiments, the ex vivo immunization method of the invention is used to treat or prevent a wide range of disorders including infectious diseases and cancer.

Compositions

The present invention provides a bacterial cell and a bacterial minicell which have the ability to deliver a compound of interest. For example, the bacterial cell and bacterial minicell of the invention has the ability to secrete a compound contained therein, and in certain instances, deliver the compound into a recipient cell. In certain embodiments, the bacterial cell of the invention is replication deficient. In certain instances, the replication-deficient bacterial cell produces a bacterial minicell that, while not containing the bacterial chromosome, contains one or more components necessary for secreting and delivering a compound. For example, in one embodiment, the bacterial minicell comprises one or more components of the T3SS.

The present invention is not limited to the particular type or strain of bacteria. Rather, any bacterial strain which contains a type III secretion system is encompassed in the present invention. In one embodiment, the bacterial cell and bacterial minicell are of the *Salmonella enterica* serovar *typhimurium* (*S. typhimurium*) strain. Other exemplary bacterial strains include, but are not limited to, *Shigella* spp., *Yersinia* spp., *Escherichia coli*, and *Pseudomonas* spp. In certain embodiments, the bacterial cell and bacterial minicell of the invention comprise one or more components of the T3SS. In certain embodiments, the T3SS is encoded by the *salmonella* pathogenicity island-1. However, the invention is not limited to any particular type III secretion system encoded by any particular pathogenicity island.

In one embodiment, the composition of the invention comprises a replication-deficient bacterial cell. For example, in certain embodiments, the bacterial minicell of the invention is derived from replication-deficient bacteria. In one embodiment, the bacterial cell of the invention is modified to render the bacterial cell replication deficient. For example, in one embodiment, the bacterial cell is genetically modified to comprise a mutation which renders the cell replication deficient. For example, the cell may be modified to comprise in mutation in genes including, but not limited to, minA, minB, minC, minD, ftsA, ftsZ, and zipA. For example, in one embodiment, the bacterial cell comprises mutant minD, which renders the bacterial cell replication deficient. In one embodiment, the bacterial cell comprises a deletion mutation in minD. In one embodiment, the bacterial cell comprises a nucleic acid sequence encoding a mutant minD. In another embodiment, the bacterial cell comprises an inhibitor of the activity, expression, or both of one or more proteins which play a role in bacterial cell replication, including, but not limited to minA, minB, minC, minD, ftsA, ftsZ, and zipA. An inhibitor of the activity, expression, or both of one or proteins which play role in bacterial cell replication includes, but is not limited to an antisense nucleic acid, siRNA, peptide inhibitor, antibody, ribozyme, small molecule, and the like. In one embodiment, the composition of the invention comprises a bacterial cell, wherein the activity, expression, or both of one or more proteins which play a role in bacterial cell replication in the bacterial cell is reduced.

In one embodiment, the composition of the invention comprises a bacterial cell modified to increase the expression of one or more T3SS components. For example, in certain embodiment, the bacterial cell of the invention is modified to express HilA, a positive transcriptional regulator of T3SS. For example, in certain embodiments, the bacterial cell of the invention is modified to comprise an isolated nucleic acid comprising an nucleic acid sequence encoding HilA. In one embodiment, the bacterial cell of the invention is modified to comprise at least one isolated nucleic acid comprising a nucleic acid sequence encoding at least one T3SS component. The at least one nucleic acid encoding the at least one T3SS component includes, but is not limited to DNA, RNA, mRNA, cDNA, and the like. Exemplary T3SS components which are encoded by the at least one nucleic acid include, but are not limited to those listed in Table 4, Table 5, and Table 6. In one embodiment, the bacterial cell of the invention is modified to express increased levels of InvB, SipB, SipC, SipD, InvE, SicA, SigE, or combinations thereof. For example, in one embodiment, the bacterial cell of the invention comprises at least one isolated nucleic acid comprising a nucleic acid sequence encoding at least one of InvB, SipB, SipC, SipD, InvE, SicA, SigE, or combinations thereof.

In one embodiment, the composition of the invention comprises a bacterial cell modified to comprise a compound of interest to be secreted. The present invention is not limited to the particular type or identity of compound of interest. Rather, the present invention encompasses a bacterial cell and bacterial minicell comprising any compound of interested desired to be secreted. Exemplary types of compounds include, but are not limited to, peptides, proteins, nucleic acids, small molecules, and the like. In one embodiment, the compound of interest is a chimera comprising a targeting domain, which directs the compound of interest to the T3SS. In certain embodiments, the targeting domain is derived from proteins that are known to be delivered by T3SS, including but not limited to SopE, SptB, SopB, and SipA. For example, in one embodiment, the compound of interest comprises SopE, or fragment thereof, which directs the compound of interest to the T3SS for secretion. In one embodiment, the compound of interest comprises the first 104 amino acids of SopE. In certain embodiments, the bacterial cell or bacterial minicell of the invention is modified to comprise the compound of interest by any method known in the art. In one embodiment, the bacterial cell or bacterial minicell of the invention are genetically modified to express the compound of interest. For example, in one embodiment, the bacterial cell or bacterial minicell comprise an isolated nucleic acid comprising a nucleic acid sequence encoding the compound of interest. The at least one nucleic acid encoding the compound of interest includes, but is not limited to DNA, RNA, mRNA, cDNA, and the like. In certain embodiments, the composition of the invention delivers the compound of interest into a recipient cell. In certain embodiments, the composition of the invention delivers the compound of interest into the recipient cell in an ex vivo environment or in an in vivo environment.

In one embodiment, the compound of interest is an antigen. As would be understood by those skilled in the art, the present invention encompasses a bacterial cell and bacterial minicell comprising any antigen known in the art. For example, the antigen may be any antigen used to induce an immunological response. In certain embodiments, the antigen comprises a peptide, nucleic acid, polysaccharide, and the like, which induces an immune response. In certain embodiments, the composition of the invention delivers an antigen into a recipient cell. In certain embodiments, the composition of the invention delivers the antigen into the recipient cell in an ex vivo environment or in an in vivo environment. As described elsewhere herein, in certain embodiments, the composition delivers the antigen into the recipient cell and induces MHC class I signaling pathways in the recipient cell. In one embodiment, the composition of the invention induces an immune response in a subject in which the recipient cell resides or in which the recipient cell is later administered.

The antigen may be derived from a virus, a fungus, or a bacterium. The antigen may be a self-antigen or an antigen associated with a disease selected from the group consisting of an infectious disease, a cancer, an autoimmune disease. In one embodiment, the antigen is a toxoid. In another embodiment, the antigen is a tumor-associated or tumor-specific antigen.

For an antigenic composition to be useful as a vaccine, the antigenic composition must induce an immune response to the antigen in a cell, tissue or mammal (e.g., a human). As used herein, an "immunological composition" may comprise an antigen (e.g., a peptide or polypeptide), a nucleic acid encoding an antigen (e.g., an antigen expression vector), a cell expressing or presenting an antigen or cellular component. In particular embodiments the antigenic composition comprises or encodes all or part of any antigen described herein, or an immunologically functional equivalent thereof. In other embodiments, the antigenic composition is in a mixture that comprises an additional immunostimulatory agent or nucleic acids encoding such an agent. Immunostimulatory agents include but are not limited to an additional antigen, an immunomodulator, an APC or an adjuvant. In other embodiments, one or more of the additional agent(s) is covalently bonded to the antigen or an immunostimulatory agent, in any combination.

In one embodiment, the composition of the invention is a vaccine delivery system comprising a bacterial cell or bacterial minicell of the invention. For example, the composition of the invention can be used to deliver an antigen to a subject for immunization or vaccination of the subject. As described herein, the vaccine delivery system safely and effectively secretes a compound of interest (e.g., antigen), which thereby induces an immune response. In certain embodiments, the vaccine delivery system of the invention comprises a bacterial minicell, which in some instances is safer than the use of a vaccine delivery system comprising live bacteria. The composition may be a vaccine delivery system for in vivo immunization and/or ex vivo therapy.

In one embodiment, the composition of the invention comprises a bacterial minicell which secretes a compound of interest. In certain embodiments, the bacterial minicell delivers the compound of interest into a recipient cell. As described elsewhere herein, in certain embodiments the bacterial cell of the invention is derived from a replication-deficient bacterial cell. For example, upon attempted replication of the replication-deficient bacterial cell, a bacterial minicell is formed. In certain embodiments, the bacterial minicell of the invention is a nanoparticle which secretes or delivers the compound of interest. In one embodiment, the bacterial minicell is not a live bacteria, thereby allowing it to be used for a safe system of compound secretion and delivery. For example, in certain embodiments, the bacterial minicell lacks the bacterial chromosome. However, in certain embodiments, one or more T3SS components are able to segregate into the bacterial minicell upon the attempted replication of the bacterial cell, thereby allowing the minicell to comprise the necessary T3SS components necessary for efficient secretion or delivery of the compound of interest.

In certain embodiments, the bacterial minicell of the invention is isolated from a bacterial cell or population of bacterial cells. As discussed elsewhere herein, the bacterial cell is not limited to any particular type or strain of bacterial cell. In certain embodiments, the bacterial cell is of the *Salmonella enterica* serovar *typhimurium* (*S. typhimurium*) strain, or derivatives thereof. The bacterial cell is cultured in any suitable method known in the art. For example, in one embodiment, the bacterial cell is grown in Luria broth (LB) containing 0.3 M NaCl to induce the expression of the T3SS. In one embodiment, culture of the bacterial cell comprises growth under low aeration conditions. In another embodiment, culture of the bacterial cell comprises agitation of the culture vessel. In certain embodiments, the LB broth contains one or more compounds which induce the expression of one or more peptides, whose expression is driven off of an inducible promoter. In certain embodiments, the bacterial minicell is generated, isolated, and purified using methods known in the art (Frazer and Curtiss, 1975, Curr Top Microbiol Immunol. 69:1-84). For example, in one embodiment, bacterial minicells are enriched in one or more centrifugation cycles, wherein the supernatant is collected while the pellets containing mostly bacterial rods are discarded. In one embodiment, the minicells are resuspended in a suitable buffer (e.g., buffered saline gelatin (BSG)). In one embodiment, the resuspended minicells are applied to a density gradient, which, in certain embodiments are subjected to further centrifugation. In one embodiment, minicell-enriched fractions are collected, pelleted, and resuspended in appropriate buffer for future use. In certain embodiments, the isolated minicells are analyzed for the presence of contaminating bacterial rods. In certain embodiment, the isolated bacterial minicell population is incubated under appropriate conditions prior to use. In one embodiment, the minicell population is incubated in a suitable buffer comprising one or more compounds which induce the expression of one or more peptides, whose expression is driven off of an inducible promoter.

In one embodiment, the invention provides a vaccine to produce an immune response. In one embodiment, the vaccine comprises a bacterial minicell, as described herein. In one embodiment, the vaccine comprises an APC comprising a minicell-delivered antigen. In one embodiment, the vaccine comprises an activated T cell, activated via an APC comprising a minicell-derived antigen. In certain embodiments, the vaccine comprises a cellular component (e.g., APC, T cell, etc.) that was modified ex vivo. For example, in certain embodiments, the vaccine comprises an APC or T cell that was isolated from a subject to be vaccinated. In one embodiment, the APC is modified ex vivo to comprise a desired antigen, as delivered by the minicell of the invention.

In certain embodiments, the vaccine of the invention induces an immune response directed against a desired antigen. As described elsewhere herein, a bacterial minicell has the ability to deliver any antigen to an APC and to the MHC class I signaling pathway. In one embodiment, the vaccine of the invention induces an immune response to treat or prevent a disorder associated with the desired antigen. In certain embodiments, the vaccine comprises an adjuvant to enhance the immunogenicity of the vaccine.

Vectors

In certain embodiments, the composition of the invention is modified to increase the expression of one or more T3SS components. Exemplary T3SS components include, but are not limited to, InvB, SipB, SipC, SipD, InvE, SicA, and SigE, as well as other components listed herein in Table 4, Table 5, or Table 6. In one embodiment, the composition of the invention is modified to express a peptide to be secreted by the composition. In certain embodiments, the composition of the invention is genetically modified to comprise an isolated nucleic acid encoding peptides or proteins described herein. For example, in certain embodiments, the composition of the invention comprises one or more expression vectors which comprise a nucleic acid sequence encoding at least one of the peptides or proteins described herein.

The nucleic acids encoding the peptide or combinations of peptides of the invention can be incorporated into suitable vectors, including plasmid vectors capable of encoding genetic information. Such vectors are well known in the art and are therefore not described in detail herein. The nucleic acids or the vectors containing them usefully can be transferred into a bacterial cell or bacterial minicell of the invention.

In one embodiment, the invention includes a nucleic acid sequence encoding one or more peptides of the invention operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into the bacterial cell or bacterial minicell with concomitant expression of the exogenous DNA in the bacterial cell or bacterial minicell, such as those methods described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York). The incorporation of a desired polynucleotide into a vector and the choice of vectors is well-known in the art as described in, for example, Sambrook et al. (2012, Molecular Cloning: A Laboratory Manual, Cold Spring Harbor Laboratory, New York), and Ausubel et al. (1997, Current Protocols in Molecular Biology, John Wiley & Sons, New York).

The polynucleotide can be cloned into a number of types of vectors. However, the present invention should not be construed to be limited to any particular vector. Instead, the present invention should be construed to encompass a wide plethora of vectors which are readily available and/or well-known in the art. For example, the polynucleotide of the invention can be cloned into a vector including, but not limited to a plasmid, a phagemid, a phage derivative, and a cosmid. Vectors of particular interest include expression vectors that can partition to minicells such as those derived from the ColE replicon and derivatives.

In specific embodiments, the expression vector a bacterial plasmid vector. Numerous expression vector systems exist that comprise at least a part or all of the compositions discussed above. Prokaryote-based systems can be employed for use with the present invention to produce polynucleotides, or their cognate polypeptides. Many such systems are commercially and widely available.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, inducible, and/or useful under the appropriate conditions to direct high level expression of the introduced DNA segment, such as is advantageous in the large-scale production of recombinant proteins and/or peptides. The promoter may be heterologous or endogenous.

The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to an arabinose promoter, rhamnose promoter, metallothionine promoter, a glucocorticoid promoter, a progesterone promoter, and a tetracycline promoter.

In order to assess the expression of the nucleotide sequences encoding the peptide or combinations of peptides of the invention, the expression vector to be introduced into a bacterial cell or bacterial minicell can also contain either a selectable marker gene or a reporter gene or both to facilitate identification and selection of expressing cells or minicells from the population of cells or minicells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the bacterial cell or bacterial minicell of the invention.

Suitable reporter genes may include genes encoding luciferase, beta-galactosidase, chloramphenicol acetyl transferase, secreted alkaline phosphatase, or the green fluorescent protein gene (see, e.g., Ui-Tel et al., 2000 FEBS Lett. 479:79-82). Suitable expression systems are well known and may be prepared using well known techniques or obtained commercially.

In the context of an expression vector, the vector can be readily introduced into the bacterial cell or bacterial minicell of the invention by any method in the art. For example, the expression vector can be transferred by physical, chemical or biological means Regardless of the method used to introduce exogenous nucleic acids into a bacterial cell or bacterial minicell of the invention, in order to confirm the presence of the recombinant DNA sequence in the bacterial cell or bacterial minicell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Pharmaceutical Compositions

The present invention also provides pharmaceutical compositions comprising one or more of the compositions described herein. Formulations may be employed in admixtures with conventional excipients, i.e., pharmaceutically acceptable organic or inorganic carrier substances suitable for administration to the wound or treatment site. The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., other analgesic agents.

Administration of the compositions of this invention may be carried out, for example, by parenteral, by intravenous, intratumoral, subcutaneous, intramuscular, or intraperitoneal injection, or by infusion or by any other acceptable systemic method.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

In an embodiment, the composition includes an antioxidant and a chelating agent that inhibits the degradation of one or more components of the composition. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the composition of the invention in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid.

Methods of Delivering a Compound of Interest

In one embodiment, the present invention provides a method for secreting a compound of interest. In one embodiment, the present invention provides a method for delivering a compound of interest to a recipient cell. As described herein, the present invention provides a bacterial minicell which safely and effectively secretes and delivers any compound of interest. The present method is not limited to any particular compound. Rather, the present method encompasses the secretion or delivery of any type of compound, including, but not limited to, a peptide, protein, nucleic acid, small molecule, and the like. In certain embodiments, the compound of interest, delivered by way of the present method, is a chimera, wherein the chimera comprises a targeting domain which targets the chimera to the T3SS. In certain embodiments, the targeting domain is derived from proteins that are known to be delivered by T3SS, including but not limited to SopE, SptB, SopB, and SipA.

In certain embodiments, the method comprises providing a bacterial minicell comprising the compound of interest. For example, in certain embodiments, the bacterial minicell is genetically modified to comprise an isolated nucleic acid comprising a nucleic acid sequence encoding the compound of interest. In one embodiment, the bacterial minicell is derived from a bacterial cell.

As described elsewhere herein, in certain instances replication-deficient bacterial cells produce achromosomal bacterial minicells, which demonstrate the ability to safely and effective secrete and deliver a compound of interest. In certain embodiments, the bacterial minicell is isolated from a heterogenous population of bacterial cells and bacterial minicells. Exemplary methods of isolating and purifying bacterial minicells are described elsewhere herein.

In one embodiment, the method of the invention allows for secretion of the compound of interest out of the bacterial minicell of the invention into the extracellular space. For example, in an in vitro or ex vivo environment, the compound of interest is secreted into culture media, buffer, or other solution surrounding the minicell. In another embodiment, the method provides direct delivery of the compound of interest into a eukaryotic cell, including for example an APC. For example, in certain embodiments, the bacterial minicell of the invention injects the compound of interest into a recipient eukaryotic cell. In another embodiment, the method provides secretion of the compound of interest in an in vivo environment. For example, in one embodiment, the method comprises administering the bacterial minicell to a subject, which thereby allows for secretion of the compound of interest into the subject. For example, in certain embodiments, the compound of interest is secreted into the blood or other body tissue of the subject.

In one embodiment, the method of the invention provides for the delivery of the compound of interest into a recipient cell. For example, in certain embodiments, the method comprises contacting the recipient cell with a compound of interest secreted by the bacterial minicell. In certain embodiments, the bacterial minicell is modified such that it comprises the compound of interest, which it then secretes and delivers to a recipient cell. In certain embodiments, the recipient cell is contacted directly contacted to the minicell in order to facilitate the secretion and delivery of the compound of interest from the minicell into the recipient cell. The present invention is not limited to any particular type of recipient cell. Rather, any type of recipient cell, including, but not limited to, a prokaryotic ell, a eukaryotic cell, a mammalian cell, and the like. In certain embodiments, the recipient cell is an APC. As described elsewhere herein, the bacterial minicell of the invention is capable of delivering an antigen into an APC, which, in certain instances delivers the antigen into the class I antigen presentation pathway.

Antigen Presenting Cell Therapy

The present invention also provides methods of inducing an immune response in a subject comprising delivering an antigen from a bacterial minicell to an APC. In certain embodiments, the method comprises providing an APC and contacting (stimulating) them in vitro, ex vivo or in vivo with an antigen secreted by a bacterial minicell of the invention, wherein the bacterial minicell comprises the antigen and delivers the antigen into the APC. In certain embodiments, the antigen is delivered to the APC in the body of the subject. In certain embodiments, administration of the minicell to the subject results in delivery of the antigen into an APC and T cell activation in the subject. In one embodiment, the minicell directly injects the antigen into the APC. In one embodiment, the minicell secretes the antigen.

In another embodiment, an APC of the subject is isolated from the subject, the antigen is delivered to the APC outside of the body of the subject, and the APC comprising the delivered antigen is later administered to the subject. In certain embodiments, administration of the derived APC comprising the minicell-delivered antigen to the subject, induces T cell activation in the subject.

In certain embodiments, the delivered antigen is in the form of a peptide, protein, nucleic acid, small molecule, or the like. For example, in certain embodiments, the antigen is a peptide which is processed by MHC Class I or Class II signaling pathways. In another embodiment, the antigen is a nucleic acid which undergoes transcription, translation, or both in the APC to produce a protein, which is then processed by MHC Class I or Class II signaling pathways.

In one embodiment, the derived APC comprising the minicell-delivered antigen are used in the context of an ex vivo therapeutic method, in which the APC and desired T cells or peripheral blood mononuclear leukocytes are contacted (stimulated) in vitro, and, after inducing T cell activation, the cells are returned to the subject. For example, the method may include the steps of: collecting APCs from a subject, contacting the APCs with an antigen secreted by a bacterial minicell, mixing the APCs with the desired T cell type and co-culturing so as to induce the T-cells, and collecting the T cells from the co-culture.

The present invention encompasses administering as a vaccine to a subject a bacterial minicell comprising a desired antigen; an APC comprising the minicell-delivered antigen; or an activated T cell activated by an APC comprising the minicell-delivered antigen.

The present invention provides compositions and methods for stimulating APC, preferably dendritic cells (DCs), in the context of immunotherapy to stimulate the immune response in a subject. DCs can be manipulated by loading them with one or more desired antigens by contacting them with the desired antigens secreted by a bacterial minicell of the invention.

In one embodiment, the invention includes a method for inducing a T cell response in a subject. The method comprises administering to the subject an APC, such as a DC, wherein the APC has been activated by contacting the APC with one or more desired antigens secreted by one or more bacterial minicells, thereby generating an antigen-loaded APC.

In one embodiment, the invention relates to APCs comprising minicell-delivered antigens and methods for their use to, inter alia, expand a desired T cell, to activate T cells, to expand specific T cell, as well as numerous therapeutic uses relating to expansion and stimulation of T cells using the APC.

The present invention relates to the discovery that an APC contacted with an antigen secreted by a minicell of the invention can be used to induce activation or priming of a T cell. The APCs comprising the minicell-delivered antigen are useful for eliciting an immune response against the desired antigen. Accordingly, the APCs can be used to treat a disease associated with the antigen, including but not limited to infectious diseases and cancer.

A skilled artisan would also readily understand that the APC can be contacted with the minicell-secreted antigen for a time sufficient to promote presentation of desired antigen on the surface of the APC. In certain embodiments, the minicell-delivered antigens are digested into small peptide fragments by the APC and eventually carried to and presented on the APC surface.

The invention includes a method for specifically expanding a T cell population subset. More particularly, the method comprises contacting a population of T cells comprising at least one T cell of a subset of interest with an APC capable of expanding that T cell. One skilled in the art would understand, based upon the disclosure provided herein, that T cell subsets include T helper ($T_{H1}$ and $T_{H2}$) CD4 expressing, cytotoxic T lymphocyte (CTL) (Tc1 or Tc2) T regulatory ($T_{REG}$), $T_{C/S}$, naive, memory, central memory, effector memory, and gamma delta T cells. Therefore, cell populations enriched for a particular T cell subset can be readily produced using the methods of the invention.

The present invention includes a method of enhancing the immune response in a mammal comprising the steps of contacting one or more lymphocytes with an antigenic composition, wherein the antigen is presented by an immune cell, such as an APC. The enhanced immune response may be an active or a passive immune response. The response may be part of an adoptive immunotherapy approach in which APCs, such as dendritic cells, B cells or monocytes/macrophages, are obtained from a subject (e.g., a patient), then pulsed with a composition comprising an antigenic composition (i.e., contacted with a desired antigen secreted by the bacterial minicell), and then administering the APC to a subject in need thereof. The present invention is partly based upon the discovery that a bacterial minicell retains the capability of delivering a desired antigen to an APC, thereby "pulsing" the APC and forming a minicell-delivered antigen-loaded APC.

In certain embodiments, the method of the invention comprises ex vivo immunization and/or in vivo therapy in a subject. In one embodiment, the subject is a mammal. Preferably, the mammal is a human.

In certain embodiments, ex vivo immunization, comprises in vitro pulsing of the APC by contacting the APC with a minicell-secreted antigen. Ex vivo procedures are well known in the art and are discussed more fully below. Briefly, cells are isolated from a subject (preferably a human) and contacted with the desired antigen secreted by the minicell to produce an antigen-loaded APC. The antigen-loaded APC can be administered to a recipient to provide a therapeutic benefit. The recipient may be a human and the antigen-loaded APC can be autologous with respect to the recipient. Alternatively, the APC can be allogeneic, syngeneic or xenogeneic with respect to the recipient.

In addition to using a cell-based vaccine in terms of ex vivo immunization, the present invention also provides compositions and methods for in vivo immunization to elicit an immune response directed against an antigen in a patient.

With respect to in vivo immunization, the present invention provides a use of a bacterial minicell modified to express a desired antigen to deliver the desired antigen to an APC of a subject in vivo. As such, a vaccine useful for in vivo immunization comprises at least a minicell component, wherein the minicell component is able to deliver an antigen to an APC of the subject. In certain embodiments, delivery of the antigen elicits an immune response in the subject.

Treatment Methods

In certain embodiments, the present invention provides a method of treating or preventing a disorder associated with an antigen. Exemplary disorders treated or prevented by way of the present method include, but are not limited to, infectious diseases (e.g., bacterial infections, viral infections, and fungal infections) and cancer. The invention provides the eliciting of an immune response for the treatment and prevention of disorders including, but not limited to cancer and infectious diseases. In one embodiment, the disorder is treated or prevented by in vivo administration of a bacterial minicell modified to comprise a desired antigen in order to elicit an immune response against the antigen in the subject. In another embodiment, the disorder is treated or prevented by administering an ex vivo derived APC comprising a minicell-delivered antigen in order to elicit an immune response against the antigen in the subject. In another embodiment, the disorder is treated or prevented by administering an activated T cell, activated ex vivo by an ex vivo derived APC comprising a minicell-delivered antigen in order to elicit an immune response against the antigen in the subject.

In one embodiment, the subject has a type of cancer which expresses a tumor-specific antigen. In accordance with the present invention, a bacterial minicell can be modified to comprise a tumor-specific antigen. In certain instances administration of the bacterial minicell comprising the tumor-specific antigen; an APC comprising the minicell-delivered tumor-specific antigen; or activated T cell activated by the APC comprising the minicell-delivered tumor-specific antigen to a subject in need thereof, results in an improved therapeutic outcome for the subject, evidenced by, e.g., a slowing or diminution of the growth of cancer cells or a solid tumor which expresses the tumor-specific antigen, or a reduction in the total number of cancer cells or total tumor burden.

In one embodiment, the subject has been diagnosed as having a viral, bacterial, fungal or other type of infection, which is associated with the expression of a particular antigen, e.g., a viral antigen. In accordance with the present invention, a bacterial minicell can be modified to comprise an antigen. In certain instances administration of the bacterial minicell comprising the antigen; an APC comprising the minicell-delivered antigen; or activated T cell activated by the APC comprising the minicell-delivered antigen to a subject in need thereof, results in an improved therapeutic outcome for the subject, evidenced by a slowing in the growth of the causative infectious agent within the subject and/or a decrease in, or elimination of, detectable symptoms typically associated with the particular infectious disease.

In either situation, the disorder or disease can be treated by administration of the bacterial minicell, APC, or activated T-cell, described herein. The present invention provides a means to generate a protective immune response to the antigen in the subject.

Administration of the bacterial minicell, APC, or activated T-cell, as described herein, may be continuous or intermittent, depending, for example, upon the recipient's physiological condition, whether the purpose of the administration is therapeutic or prophylactic, and other factors known to skilled practitioners. The administration of the bacterial minicell, APC, or activated T-cell may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

Subjects to which administration of the compositions of the invention is contemplated include, but are not limited to, humans and other primates, mammals including commercially relevant mammals such as non-human primates, cattle, pigs, horses, sheep, cats, and dogs.

Compositions of the present invention may be administered in a manner appropriate to the disease to be treated (or prevented). The quantity and frequency of administration will be determined by such factors as the condition of the subject, and the type and severity of the subject's disease, although appropriate dosages may be determined by clinical trials.

When "an immunologically effective amount," "an anti-tumor effective amount," "an tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject).

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the compositions of the present invention are administered to a patient by intradermal or subcutaneous injection. In another embodiment, the compositions of the present invention are preferably administered by i.v. injection.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

Engineering the Type III Secretion System in Non-replicating Bacterial Minicells for Antigen Delivery Type III protein secretion systems are being considered for vaccine development since virtually any protein antigen can be engineered for delivery by these nanomachines into the class I antigen presentation pathway to stimulate antigen-specific CD8+ T cells (Russmann et al., 1998, Science, 281: 565-568; Chen et al., 2006, Infect Immun, 74: 5826-5833). However, a limitation in the use of these prior systems is that they requires live virulence-attenuated bacteria, which may preclude its use in certain populations such as children and the immunocompromised.

To overcome some of the limitations of virulence-attenuated bacterial antigen delivery vectors while retaining some of its benefits, it was sought to engineer the T3SS in a non-replicating antigen-delivery system. As an alternative to a synthetic system, the present studies demonstrate a strategy to engineer bacterial minicells with the capacity to deliver heterologous proteins through the *Salmonella typhimurium* T3SS encoded within its pathogenicity island 1 (SPI-1). Bacterial minicells result from aberrant cell division and although they lack chromosomal DNA they have the capacity to synthesize proteins and sustain a proton gradient (Frazer and Curtiss, 1975, Curr Top Microbiol Immunol. 69:1-84). In addition, these nanoparticles have immune adjuvant capacity (Giacalone et al., 2006, Vaccine 24:6009-6017) since they retain most of the bacterial components capable of stimulating innate immune receptors (Palm and Medzhitov, 2009, Immunol Rev. 227:221-233). Described herein is the engineering of the *Salmonella typhimurium* type III secretion system in achromosomal, non-replicating nanoparticles derived from bacterial minicells. The engineered system is shown to be functional and capable of delivering heterologous antigens to the class I antigen presentation pathway stimulating immune responses both in vitro and in vivo. This antigen delivery system offers a novel approach for vaccine development and cellular immunotherapy.

The materials and methods employed in this experimental example are now described.

Bacterial Strains and Growth Conditions

All bacterial strains used in this study are derivatives of *Salmonella enterica* serovar *typhimurium* (*S. typhimurium*) SL1344 and are listed in Table 1. The minD::cat mutant allele was introduced into *S. typhimurium* as previously described (Kaniga et al., 1994, Mol. Microbiol. 13:555-568). All plasmids used in this study were constructed using standard recombinant DNA techniques and are detailed in Table 2. All *S. typhimurium* strains were grown in Luria broth (LB) containing 0.3 M NaCl to induce the expression of the T3SS encoded on the *Salmonella* pathogenicity island-1 (SPI-1).

Minicell Purification

Figure 8:
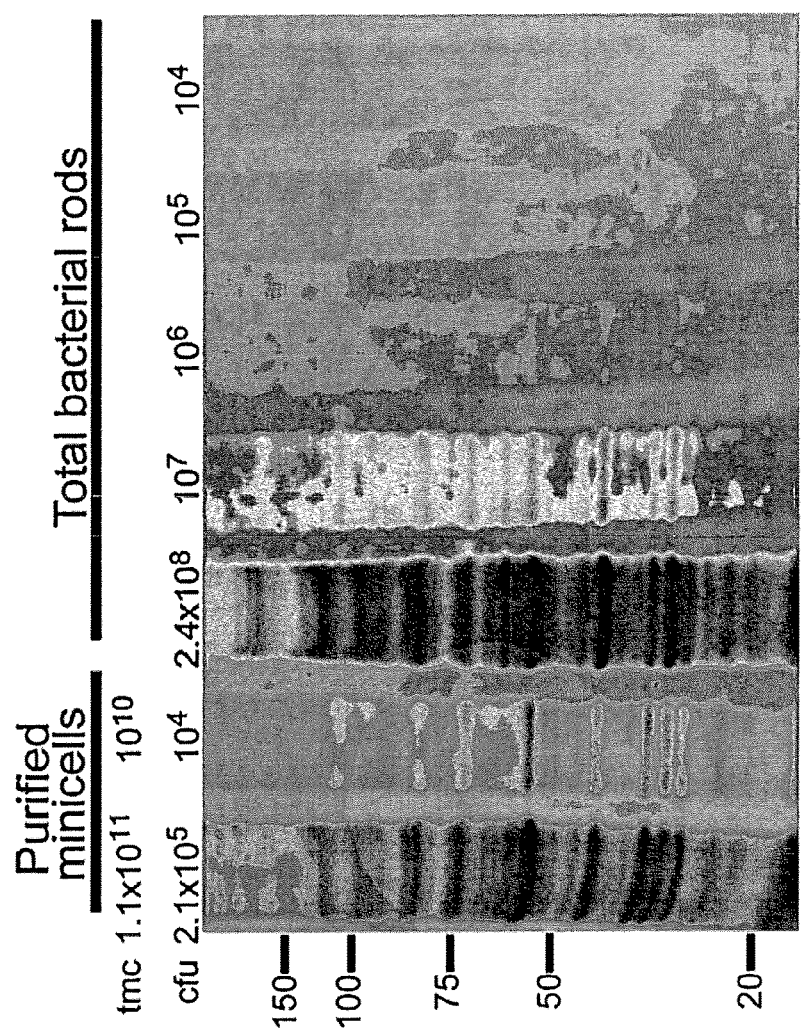
FIG. 8 is an image depicting the comparison of lysates prepared from minicells and rods at the indicated concentrations. The number of minicells is indicated as total minicell count (tmc) and the number of rods is indicated as colony forming units (cfu). These results indicate that the potential contribution of rod contaminants in the minicell samples to the total amount of protein is negligible.
Figure 9:
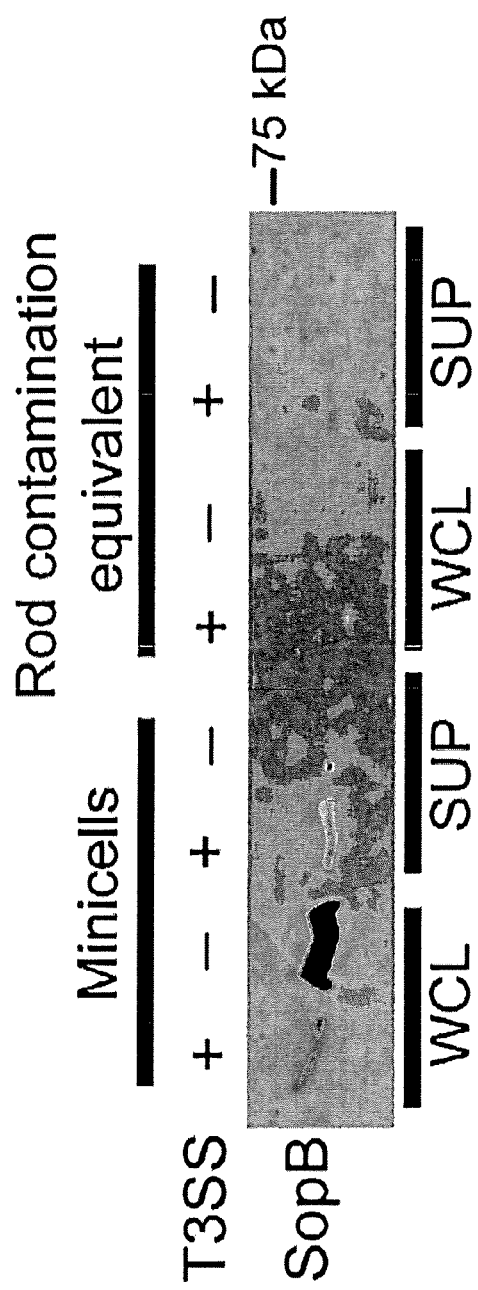
FIG. 9 is an image depicting the relative contribution of rod-derived material to the purified minicell preparation. Comparison of the levels of SopB in whole cell lysates (wcl) and supernatants (sup) obtained from minicell preparations and from an equivalent number of rods present as contaminants in the minicell preparation. These results indicate that the rod contamination does not significantly contribute to the signal observed in the minicell preparation.
Figure 10:
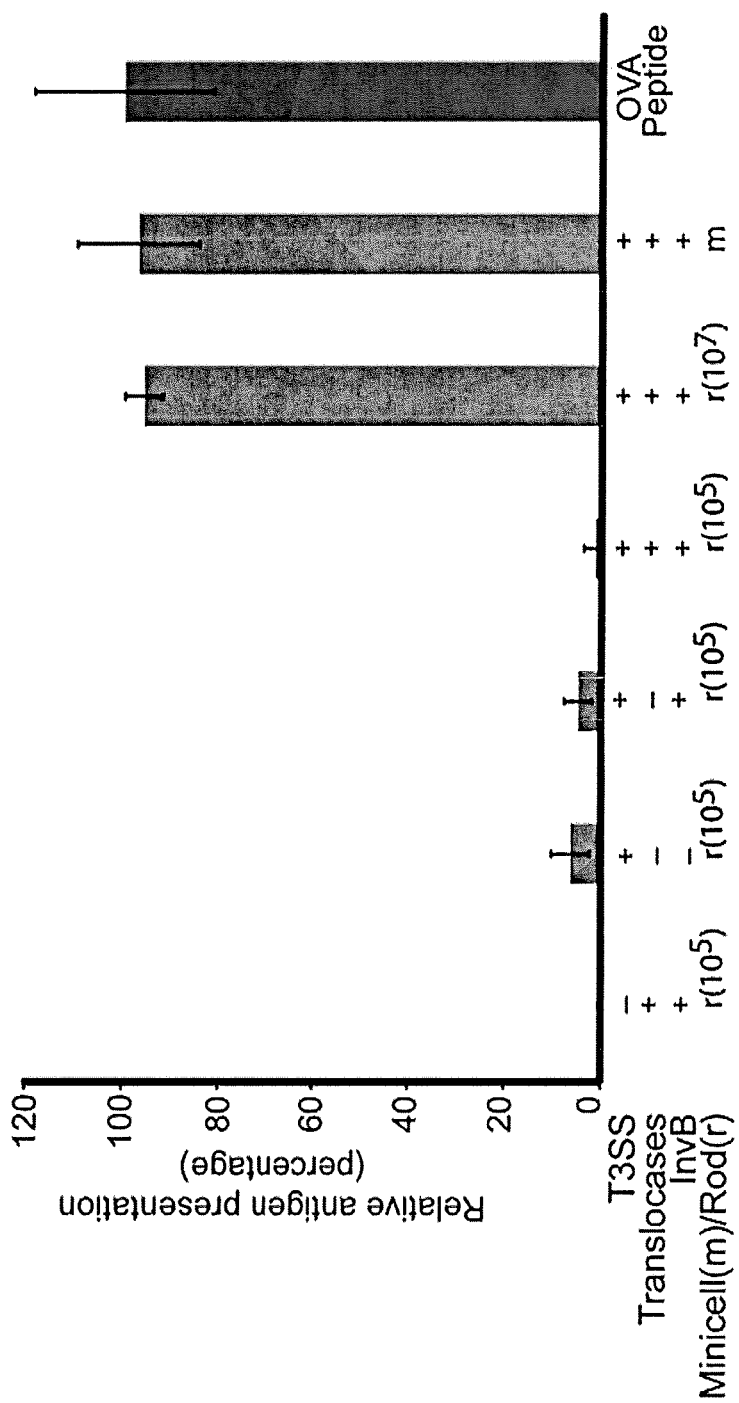
FIG. 10 is a graph demonstrating that bacterial rod cells in equivalent numbers to those present in minicell preparations used in the antigen presentation assay did not elicit a response. RMA cells (C57BL/6 mouse hybridomas) were pulsed for 3 hours with an equivalent number of wild type or T3SS-defective (ΔinvA) S. typhimurium cells (i.e. $10^5$) to those present in the minicell preparation. In addition, RMA cells were pulsed with the minimal number of bacterial rods ($10^7$) necessary to stimulate a response in this assay as well as with a minicell preparation ($10^{11}$) for comparison. After pulsing, RMA cells were fixed, and used as APCs in a B3Z T-cell activation assay as described elsewhere herein. Values represent the levels of antigen presentation based on the β-galactosidase activity detected in the B3Z-T cell hybridoma reporter and are normalized relative to the values of the OVA peptide positive control, which was considered 100%. The values are the mean±standard deviation of three independent experiments.

Minicells were purified using protocols adapted from previously published methods (Frazer and Curtiss, 1975, Curr Top Microbiol Immunol. 69:1-84) with several modifications (FIG. 5). Briefly, a 500 ml culture of a minD::cat mutant strain was grown under low aeration and agitation until an OD at $A_{600}$ of 1.1 was reached. Minicells were subsequently enriched in a series of two low-speed centrifugations at 2,000 g in which the supernatants were collected while the pellets containing mostly bacterial rods were discarded. Minicells were recovered by a final centrifugation for 30 min at 10,000 g, resuspended in a solution of buffered saline gelatin (BSG) and applied to the top of a continuous 5-20% iodixanol (OptiPrep™, Axis-Shield PLC, Scotland) density gradient formed using the gradient forming function of the Gradient Station™ (Biocomp Instruments; Fredericton, NB, Canada) in SW28 (Beckman Coulter) tubes. Gradients were subjected to 20 min of centrifugation at 2,000 g in a Beckman Coulter ultracentrifuge. After centrifugation, minicell-enriched fractions were collected using the fraction collection feature of the Gradient Station™ (Biocomp Instruments; Fredericton, NB, Canada) in 1.5 ml aliquots. Minicells in the different fractions were pelleted at 18,000 g and resuspended in the appropriate buffer for further usage. Minicells suspended in glycerol were enumerated using DIC microscopy on a CELL-VU® disposable slide that contains a chamber of a known depth of 20 µm. The number of contaminating rods in the purified minicell fractions was determined by counting the colony forming units of serial dilutions of the different fractions. The outlined protocol yielded minicells with a diameter of 200 to 550 nm (with an average of 394±90 nm). The average yield of purified minicells was $1.67±0.70×10^{12}$ minicells per preparation. The contamination from bacterial rods was estimated to be 1 rod in $10^6$ minicells, which represents 0.001% of the total protein mass present in the minicell preparation (FIG. 8). This low level of contaminating rods did not impact any of the assays conducted with minicells since proteins potentially secreted by this number of rods would be well below detection in secretion (FIG. 9) or antigen presentation (FIG. 10) assays.

SDS-Polyacrylamide Gel Electrophoresis and Immunoblotting

Lysates were solubilized in Laemmli buffer and then separated on sodium dodecyl sulfate (SDS)-10% or 15% polyacrylamide gels. The gels were subsequently visualized by Coomassie brilliant blue staining. For immunoblotting, proteins were transferred onto PVDF or nitrocellulose membranes and treated with mouse monoclonal antibodies against the relevant proteins or epitope tags as indicated. Protein bands were visualized using an Odyssey infrared imaging system (LI-COR Biosciences). When comparing protein concentrations between different samples by immunoblot, all samples were first normalized to the detected integrated intensity of cell lysates after Coomassie blue staining using the Odyssey infrared imaging system (FIG. 7).

Mass Spectrometry Analysis

Equivalent protein concentrations of minicell and bacterial rod proteins from a parental strain grown under SPI-1 T3SS-inducing conditions were briefly separated on a 10% SDS-PAGE gel and processed for liquid chromatography-tandem mass spectrometry (LC-MS/MS) to identify peptides as previously described (Lara-Tejero et al., 2011, Science 331:1188-1191). All raw data from the MS/MS scans was processed and searched against the *Salmonella* database with MASCOT (Matrix Science Ltd. London, UK). The peptide and protein assignments from MASCOT were filtered to retain only those identifications with MASCOT scores above extensive homology. Relative protein abundance was determined by the spectral counting method (Liu et al., 2004, Anal Chem 76: 4193-4201). Experiments were carried out in triplicate with three biological replicates for each experimental condition unless noted otherwise. Data between technical replicates in a single biological sample were normalized and spectral counts for each technical replicate in individual biological replicates were averaged. All biological replicates with a spectral count of less than one were arbitrarily assigned a value of 0.5 to reflect the limits of detection. Spectral counts were logarithmically transformed to obtain a binomial distribution then statistically evaluated using a paired, two-tailed t-test to determine significant differences between protein relative abundance (Gonzalez-Alba et al., 2011, J Virol, 85: 10755-10763) in minicell versus bacterial rod samples. Due to their different ratio of membrane vs. cytosol, minicells were found to be relatively enriched in membrane proteins (median 2.0 fold) and depleted in cytoplasmic proteins (median −1.8 fold). The prediction of protein subcellular localization was carried out with PSORT. Therefore, the relative abundance of membrane and cytoplasmic proteins was corrected to reflect these differences. The correction factor introduced was −2.0 for predicted membrane proteins and +1.8 for predicted cytoplasmic proteins. For comparison of abundance of T3SS proteins in minicells and rods obtained from a parental strain overexpressing hilA, all samples were obtained from cultures grown in the presence of 0.02% rhamnose.

Electron Microscopy

Minicells were purified from bacterial rods grown under SPI-1 T3SS-inducing conditions. After purification, the minicells were subsequently osmotically-shocked and visualized under the electron microscope following a protocol adapted from Kubori et al. (1998, Science 280:602-605).

Immunofluorescence Staining

Purified minicells were isolated from bacterial rods grown to an optical density measured at 600 nm (OD600) of 1.1. These minicells were serially diluted and spun at 750 g onto acid washed, poly-D lysine coated coverslips and fixed for 30 min in a 4% paraformaldehyde solution in PBS. Coverslips were washed and incubated with a solution of 3% bovine serum albumin in PBS for 30 min. Minicells were subsequently labeled with rabbit polyclonal anti-*S. typhimurium* lipopolysaccharide (Difco Laboratories) at a 1:2,000 dilution or mouse monoclonal anti-Flag M2 (Sigma) at a 1:10,000 dilution for 1 hour. Minicells were then labeled with secondary anti-rabbit antibody conjugated to Alexa 594, an anti-mouse antibody conjugated to Alexa 488 at a dilution of 1:2,000, and DAPI. Images were captured with a fluorescence microscope (Nikon Diaphot) equipped with a Princeton Instruments CCD camera and analyzed using ImageJ (U.S. National Institutes of Health, Bethesda, Md., USA). The proportion of minicells expressing SipD on their surface was determined after overlaying captured images showing the LPS stain, the SipD stain, and the DIC image of the minicells. For each minicell sample, three different experiments (i.e., biological replicates) were used for immunofluorescence analysis and two different fields of view were analyzed per biological replicate counting a minimum of 4,000 minicells for each condition.

Analysis of T3SS Function in Bacterial Minicells

Minicells were purified from a strain carrying plasmids expressing SopB and its chaperone SigE under the control of an arabinose-inducible promoter (pBAD-sopB-sigE) and (Patel et al., 2009, Cell 137:283-294) a plasmid expressing HilA. Purified minicells were then incubated for 3 hours at 37° C. in the presence of the 0.1% arabinose to allow further expression of the SopB construct. Minicells were subsequently pelleted at 20,000×g for 30 min at 4° C., supernatants removed and filtered through a 0.22 µm-pore-size filter to remove any remaining minicells. Proteins from this supernatant were precipitated by adding 0.1% sodium deoxycholate and 10% trichloroacetic acid. After incubation at 4° C. overnight, proteins were recovered by centrifugation at 20,000 g for 20 min. Pellets were washed in acetone, dried and resuspended in Laemmli buffer. Polyacrylamide gel electrophoresis and Western blot analysis of the recovered supernatant proteins was carried out as described above.

Minicell-mediated protein translocation into cultured cells was assayed as previously described (Collazo and Galán, 1997, Mol. Microbiol. 24:747-756) with some modifications. Purified minicells were added to Henle-407 cells grown to ~80% confluency in 15 cm tissue culture dishes in the presence of the proteasome inhibitor MG132 (to prevent effector protein degradation) and 0.2% arabinose. After 2.5 hours treatment, the supernatant and extracellular minicells were removed and centrifuged at 8,000×g for 30 min at 4° C., the supernatant was collected an filtered through a 0.22 µm-pore-size filter to remove any remaining minicells. Henle-407 cells were washed with PBS 3 times and scraped off the plates in the presence of 5 µM protease inhibitors and 0.1% Triton-X 100. The Triton-X 100 insoluble fraction was resuspended in Laemmli buffer and proteins in the extracellular supernatant and Triton-X 100 soluble fraction were precipitated by addition of ammonium sulfate (50% weight/vol final concentration), resuspended in 10M Urea, and analyzed by Western blot analysis.

Antigen Presentation Assay

Analysis of antigen delivery and subsequent CD8+ T-cell activation was carried out using an in vitro T cell activation assay adapted from previously published protocols (Chen et al., 2006, Infect Immun 74:5826-5833; Karttunen et al., 1992, Proc Natl Acad Sci USA. 89:6020-6024) with minor modifications. RMA cells (C57BL/6 mouse hybridomas) or bone marrow-derived dendritic cells (BMDCs) obtained from C57BL/6 mice were used as antigen-presenting cells after incubation with minicells isolated from various parental S. typhimurium strains. Mouse BMDCs were prepared as described previously (Salado et al., 1011, Inflammatory bowel diseases: 17: E143-144). Approximately $10^{11}$ minicells were used to deliver antigen to approximately $10^7$ RMA cells in one well of a 6 well dish in 2 ml of Dulbecco's modified Eagle's medium (DMEM) at 37° C. for 3 hours. Alternatively, $10^{10}$ minicells were incubated with $10^6$ BMDCs per well in a 24 well plate. For these experiments, the Δasd mutation (Galan et al., 1990, Gene, 94(1): 29-35) was introduced into all the S. typhimurium minicell-generating strains. The Δasd mutation renders S. typhimurium auxotrophic for L-diaminopimelic acid (DAP), which is absent in host tissues. Consequently, any small number of bacterial rods remaining in the minicell preparation will undergo rapid "DAP-less" death shortly after infection and will not contribute to the immune response. In addition to DMEM the cells were also incubated in the presence of 0.2% arabinose to induce expression from plasmids contained within the minicell. After incubation, the cells were washed three times in PBS and then fixed in 1% paraformaldehyde either for 20 min at room temperature or overnight at 4° C. After fixation of the antigen presenting cells, the cells were washed and then plated at a concentration of $2\times10^5$ in triplicate in 100 μl DMEM cultures in a 96-well dish. To each well $2\times10^5$ OVA-specific B3Z T-cell hybridoma cells were then added. This transgenic cell line expresses a T-cell receptor specific for the MHC class I immunodominant peptide of OVA, SIINFEKL (SEQ ID NO: 1). The activation of the TCR of the B3Z cells was determined by an NF-AT-dependent transcriptional reporter consisting of the IL-2 promoter fused to LacZ (Karttunen et al., 1992, Proc Natl Acad Sci USA: 89:6020-6024). After incubation for approximately 19 hours, the B3Z T cells were washed, lysed, and β-galactosidase production was measured using a chromogenic substrate, chlorophenolred-β-D-galactopyranoside (CPRG, CALBIOCHEM). Addition of the OVA peptide SIINFEKL (SEQ ID NO: 1) (1 μM, ABBIOTEC) served as a positive control and all results were normalized relative to the values obtained with the SIINFEKL (SEQ ID NO: 1) peptide.

Adoptive Transfer and Animal Immunization

Adoptive transfer experiments were carried out as previously described (Ripoll et al., 2011, Antimicrob Agents Chemother, 55: 4530-4536) with modifications. Spleens were removed from OT-1 (CD45.2/C57BL/6) mice, homogenized using a 1 mm² mesh metal strainer, and red blood cells were lysed with a hypotonic buffer (0.15M NH4 CL and 1 mM NaHCO3, pH 7.4). A total of $1-2\times10^7$ splenocytes were then injected in the tail vein of C57BL/6 (CD45.1) mice and one day later, mice were immunized by intraperitoneal administration of $1-2\times10^{10}$ minicells purified from different S. typhimurium parental strains. Minicells were pulsed for 3 hours at 37° C. in L broth containing 0.2% arabinose prior to immunization to allow SopE-OVA antigen expression. For these experiments, the Δasd mutation (Galan et al., 1990, Gene, 94(1): 29-35) was introduced into all the S. typhimurium minicell-generating strains to avoid replication of the very small number of contaminating rod cells. Three weeks after the initial immunization, mice were boosted by i.p. administration of $1\times10^7$ plaque forming units (PFUs) of recombinant Vesicular stomatitis virus expressing OVA (VSV-OVA). Five days after boosting, immunized mice were sacrificed and the spleens were removed and splenocytes prepared as described above.

For protection studies, BMDCs were prepared from Balb/c mice as outlined above, and incubated in the presence of GM-CSF with purified minicells prepared from different bacterial strains, all carrying the Δasd mutation (to prevent replication of the minor contaminating bacterial rod fraction). The BMDCs were extensively washed and applied in the tail vein of Balb/c recipient mice. Six days after BMDC transfer, mice were challenged i. v. with $7\times10^3$ cfus Listeria monocytogenes strain 10403s and sacrificed 3 days later. Spleens were removed from the sacrificed mice and c. f. u. enumerated by plating dilutions of homogenized tissues.

Measurement of OVA-Specific CD8+ T-Cell Responses

Splenocytes prepared from immunized mice were resuspended in PBS containing 0.1% BSA and added to a 96-well U-bottom plates at a concentration of $1-2\times10^6$ cells in 50 μl per well. Splenocytes were then stained with conjugated antibodies directed at CD8 (FITC) and CD45.2 (APC), using standard procedures at 4° C. (conjugated antibodies from eBioscience). Stained cells were fixed in 2.5% formaldehyde in PBS at 4° C. overnight and analyzed using a FACSCalibur flow cytometer (Becton-Dickson) and FlowJo software (Tree Star, Inc.).

TABLE 1

Bacterial strains used in this study

| Strain | Relevant genotype | References or sources |
|---|---|---|
| S. typhimurium | | |
| SL1344 | wild-type rpsL hisG | Hoiseth et al., 1981, Nature, 291: 238-239 |
| SB136 | invA::aphT | Galan et al., 1992, J Bacteriol, 17: 4338-4349 |
| SB1780 | minD::cat | (this study) |
| SB1781 | minD::cat invA::aphT | P22HTint [SB1780] => SB136 (this study) |
| SB1771 | minD::cat sipD3xF | P22HTint [SB1780] => SB1630 (Lara-Tejero and Galan, 2009, Infect Immun, 77: 2635-2642; this study) |
| SB1774 | invA::aphT minD::cat sipD3xF | P22HTint [SB136] => SB1771 (this study) |
| SB2105 | sipAM45 3xFspaO | (this study) |
| SB1790 | minD::cat sipAM45 3xFspaO | P22HTint [SB1780] => SB2105 (this study) |
| SB1400 | Δasd | Galan et al., 1990, Gene, 94: 29-35 |
| SB1777 | minD::cat Δasd | P22HTint [SB1780] => SB1400 (this study) |
| SB1788 | minD::cat invA::aphT Δasd | P22HTint [SB136] => SB1777 (this study) |

TABLE 2

Plasmids used in this study

| Plasmid Name | Relevant information | References or sources |
|---|---|---|
| pSB3504 | $p^{rhaBAD}$, Spectinomycin$^R$, hilA | Wagner et al., 2010, Proc Natl Acad Sci USA, 107: 17745-17750 |
| pSB2811 | pBAD24-sopB3xF-sigE | Patel and Galan, 2006, J Cell Biol, 175: 453-463 |
| pSB3506 | pBAD24-sopE-OVA3xF | (this study) |
| pSB3507 | pBAD24-sopE-OVA3xF invB | (this study) |
| pSB3508 | pBAD24-sopE-OVA-3xF invB invE sicA sipB sipC sipD | (this study) |
| pSB3510 | pBAD24-sopE-m45-LLO-p60 invB invE sicA sipB sipC sipD | (this study) |

TABLE 3

Antibodies used in the study

| Antibody | Source | Catalog # | Dilution |
|---|---|---|---|
| Anti-Flag (M2) | Sigma | F3165 | 1:10,000 |
| Anti-M45 | Galan laboratory | | 1:500 |
| Anti-SipB | Galan laboratory | | 1:2,000 |
| Anti-SipC | Galan laboratory | | 1:500 |
| Anti-Needle Complex | Galan laboratory | | 1:5,000 |
| Anti-mouse Dylight 680 | Pierce | PI35518 | 1:10,000 |
| Anti-rabbit Dylight 800 | Pierce | PI35571 | 1:10,000 |
| Anti-mouse HRP | Sigma | A4416 | 1:10,000 |

The results of this experimental example are now described.

Bacterial Minicells Assemble Type III Secretion Systems

Figure 6:
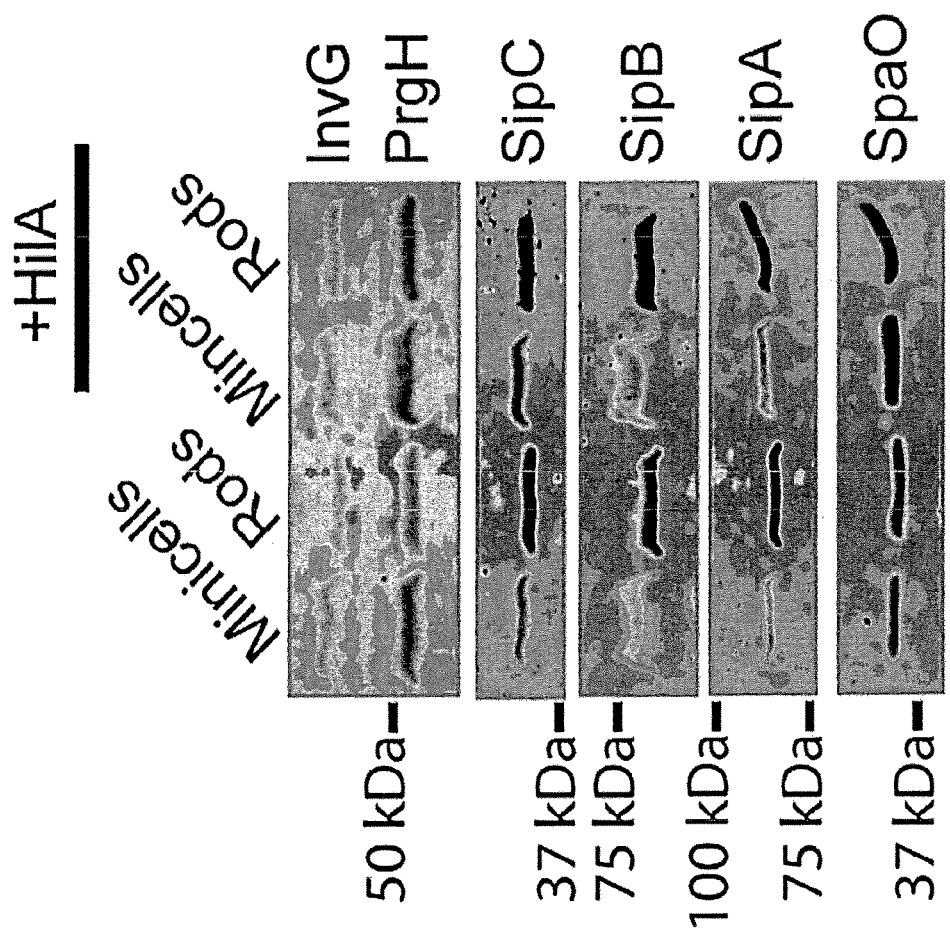
FIG. 6 is an image depicting the comparison of the levels of selected SPI-1 T3SS-associated proteins in minicells and bacterial rods from strains with or without overexpression of the SPI-1 T3SS transcriptional regulator HilA. An equal amount of protein (standardized based on the values shown in FIG. 7A) from minicell or bacterial rod lysates were analyzed by Western blot with antibodies directed to the indicated proteins.

Minicells were isolated from a *S. typhimurium* strain carrying a deletion mutation in minD (FIG. 5), which is required for proper cell division (de Boer et al., 1989, Cell 56:641-649). Loss of this gene results in aberrant cell division with the production of a large number of minicells (FIG. 1A). Highly purified minicell preparations were examined by LC-MS/MS for the presence of components of the SPI-1 T3SS. While most of the SPI-1 T3SS components were able to be detected (FIG. 1B, Table 4 and Table 5), the concentrations of T3SS-associated proteins were significantly lower compared to that of the originating bacterial cells. In particular, the protein translocases, which mediate the passage of the type III secreted proteins through the mammalian cell membrane (Collazo and Galán, 1997, Mol. Microbiol. 24:747-756), were significantly depleted in bacterial minicells. These results were confirmed by western blot analysis of selected T3SS-associated proteins (FIG. 1B, FIG. 6 and FIG. 7A). These findings indicated that although components of the SPI-1 T3SS can partition into minicells, in certain instances they might not be abundant enough to efficiently function as a protein delivery machine. To increase the levels of SPI-1 T3SS components partitioned into minicells a plasmid encoding HilA, the positive transcription regulator of the SPI-1 T3SS, expressed under a rhamnose-inducible promoter (Bajaj et al., 1995, Mol. Microbiol. 18:715-727) was introduced into the *S. typhimurium* minD strain. Studies have shown that the overexpression of HilA results in increased levels of all components of this system. LC-MS/MS analysis of minicells produced by this strain showed significantly increased levels of SPI-1 T3SS components (FIG. 1B, Table, 1, FIG. 6, FIG. 7A and Table 6). Consistent with these findings, minicells assembled T3SS needle complexes, the core structure of this secretion machine (Kubori et al., 1998, Science 280:602-605), which could be readily visualized by electron microscopy in intact minicells (FIG. 1C) or in purified needle complex preparations (FIG. 1D). These results indicate that SPI-1 T3SS components not only can partition into minicells but also can assemble into a potentially functional secretion machine.

TABLE 4

Relative Levels of T3SS-associated proteins in purified minicells
Relative Abundance†

| TTSS Protein | minicells vs rods | minicells (+HilA vs wt) |
|---|---|---|
| *Regulatory proteins* | | |
| HilA | −1.8 | 67 |
| HilD | 0.4 | ND |
| IacP | −1.3 | ND |
| InvF | −3.4* | 9.6 |
| *Structural and associated proteins* | | |
| InvA | −0.9 | 12 |
| InvC | −3.5 | 14 |
| InvG | −3.5 | 3 |
| InvH | −3.3 | 2.1 |
| PrgH | −3.6* | 5.1 |
| PrgI | −0.9 | ND |
| PrgJ | −3.3 | 4.8 |
| PrgK | −3.1 | 6.0 |
| SpaS | −3.3 | −1.9 |
| SpaP | ND | 31 |
| *Chaperone and chaperone-like proteins* | | |
| InvB | −0.13* | 2.7 |
| InvE | 0.6 | 2.0 |
| SicA | −1.0* | 1.7 |
| SicP | −2.6 | 14 |
| SigE | −0.8 | 2.3 |
| SpaO | 0.6 | 3.3 |
| OrgA | −0.3 | 6.3 |
| OrgB | 0.3 | 4.4 |
| *Secreted proteins* | | |
| AvrA | −0.1 | −1.4 |
| InvJ | −3.6* | −2.8 |
| SipA | −4.0* | 2.1 |
| SipB | −1.5 | 6.3 |
| SipC | −0.2 | 4.6 |
| SipD | −5.9* | 6.2 |
| SlrP | −8.1* | 2.9 |
| SopA | −0.8 | 5.9 |
| SopB | −1.2 | 2.8 |
| SopD | −3.9 | 43 |
| SopE | −0.5 | 3.4 |
| SopE2 | −6.9* | 14 |
| SptP | −8.7* | 2.1 |

Numbers indicate fold differences between the spectral counts of the indicated T3SS proteins (obtained by LC-MS/MS analysis) in minicells and rods (obtained from wild-type *S. typhimurium*), or between minicells obtained from wild type and a HilA overproducing strain. Negative values indicate lower levels relative to the bacterial rod sample (first column) or wild type minicell sample (second column) (see full data set in Table 5 and Table 6). *Indicates statistically significant differences (P<0.05) as determined by paired t-test. Abbreviations: ND, not determined; T3SS, type III secretion system. †Relative levels of T3SS-associated proteins in purified minicells.

TABLE 5

Spectral counts obtained by LC-MS/MS analysis of T3SS-associated proteins in minicell and rod samples from ΔminD S. typhimurium

| T3SS Protein | Spectral Counts Minicell Biological Replicates 1 | 2 | 3 | Spectral Counts Rod Biological Replicates 1 | 2 | 3 | Relative Abundance (fold difference)[1] minicells vs. rods | Adjusted Values[2] |
|---|---|---|---|---|---|---|---|---|
| AvrA | 0.5 | 0.6 | 1.3 | 0.6 | 1.0 | 8.1 | −1.9 | −0.1 |
| HilA | 9.3 | 7.0 | 2.7 | 21.1 | 23.3 | 29.7 | −3.6 | −1.8 |
| HilD | 0.5 | 1.2 | 0.7 | 0.6 | 1.0 | 4.2 | −1.4 | −4.0 |
| IacP | 0.7 | 1.0 | 0.5 | 4.3 | 1.5 | 2.5 | −3.0 | −1.3 |
| InvA | 2.3 | 2.3 | 1.8 | 2.0 | 1.3 | 4.6 | 1.1 | −0.9 |
| InvB | 38.0 | 21.9 | 27.0 | 69.1 | 57.0 | 43.5 | −1.9 | −0.1 |
| InvC | 7.7 | 6.3 | 4.7 | 7.5 | 9.3 | 16.6 | −1.5 | −3.5 |
| InvE | 0.7 | 0.8 | 0.7 | 0.6 | 0.7 | 4.2 | −1.2 | 0.6 |
| InvF | 0.5 | 0.6 | 0.5 | 3.5 | 2.0 | 3.5 | −5.2 | −3.4 |
| InvG | 48.0 | 34.4 | 40.3 | 52.0 | 65.3 | 69.0 | −1.5 | −3.5 |
| InvH | 5.0 | 3.1 | 9.0 | 9.8 | 6.0 | 7.1 | −1.3 | −3.3 |
| InvJ | 2.0 | 1.6 | 2.0 | 11.9 | 5.3 | 20.5 | −5.4 | −3.6 |
| OrgA | 3.0 | 0.8 | 2.3 | 7.8 | 4.0 | 2.8 | −2.1 | −0.3 |
| OrgB | 16.3 | 8.2 | 14.7 | 19.7 | 19.0 | 20.2 | −1.5 | 0.3 |
| PrgH | 22.7 | 19.9 | 17.0 | 35.9 | 28.7 | 32.2 | −1.6 | −3.6 |
| PrgI | 11.3 | 9.8 | 7.0 | 9.5 | 6.3 | 9.9 | 1.1 | −0.9 |
| PrgJ | 1.7 | 1.6 | 1.3 | 3.8 | 1.5 | 1.8 | −1.3 | −3.3 |
| PrgK | 27.0 | 23.4 | 25.0 | 37.3 | 24.0 | 21.6 | −1.0 | −3.1 |
| SicA | 38.0 | 26.2 | 28.7 | 111.6 | 89.7 | 66.2 | −2.8 | −1.0 |
| SicP | 0.5 | 0.6 | 1.2 | 9.0 | 7.0 | 2.1 | −4.4 | −2.6 |
| SigE | 18.0 | 16.8 | 16.7 | 83.3 | 47.0 | 28.7 | −2.6 | −0.8 |
| SipA | 21.3 | 11.7 | 49.7 | 162.5 | 118.3 | 173.0 | −5.8 | −4.0 |
| SipB | 151.7 | 54.7 | 114.7 | 445.0 | 395.7 | 273.5 | −3.3 | −1.5 |
| SipC | 66.0 | 28.5 | 93.0 | 105.0 | 92.7 | 168.1 | −2.0 | −0.2 |
| SipD | 7.0 | 3.5 | 13.0 | 61.0 | 46.7 | 64.8 | −7.7 | −5.9 |
| SlrP | 2.7 | 0.6 | 1.0 | 20.0 | 8.0 | 10.3 | −9.9 | −8.1 |
| SopA | 4.0 | 6.3 | 8.3 | 26.0 | 10.0 | 21.9 | −2.6 | −0.8 |
| SopB | 75.3 | 44.2 | 93.3 | 306.5 | 214.7 | 170.5 | −3.0 | −1.2 |
| SopD | 0.5 | 0.6 | 1.7 | 17.3 | 2.7 | 6.0 | −5.7 | −3.9 |
| SopE | 31.0 | 13.7 | 19.7 | 79.2 | 78.0 | 26.9 | −2.3 | −0.5 |
| SopE2 | 2.7 | 1.2 | 0.5 | 22.8 | 22.0 | 2.8 | −8.7 | −6.9 |
| SpaO | 11.7 | 10.9 | 9.0 | 11.9 | 14.3 | 12.4 | −1.2 | 0.6 |
| SpaS | 5.7 | 3.5 | 3.7 | 4.9 | 6.7 | 5.3 | −1.3 | −3.3 |
| SptP | 6.3 | 4.7 | 6.7 | 103.5 | 47.0 | 53.1 | −10.5 | −8.7 |

[1]Relative abundance was determined by comparing the average spectral counts of rod and minicell samples.
[2]Values have been adjusted to account for the different ratio of membrane versus cytoplasmic content in the minicells.

TABLE 6

Spectral counts obtained by LC-MS/MS analysis of T3SS-associated proteins in minicell and rod samples from ΔminD S. typhimurium overexpressing the T3SS positive transcription regulator HilA.

| Protein | Spectral Counts Minicells | Rods | Minicells (+HilA) | Rods (+HilA) | Relative Abundance (Fold Difference)[1] Minicells (+HilA) versus minicells | Minicells (+HilA) versus rods | Minicells (+HilA) versus rods (+HilA) |
|---|---|---|---|---|---|---|---|
| AvrA | 0.9 | 3.2 | 0.7 | 2.2 | −1.4 | −4.9 | −3.3 |
| HilA | 1.3 | 25.7 | 86.1 | 175.2 | 67.5 | 3.4 | −2.0 |
| HilD | 0.5 | 4.0 | 0.7 | 3.2 | 1.2 | −6.1 | −4.9 |
| IacP | 0.5 | 0.7 | 0.7 | 2.2 | 1.2 | −1.0 | −3.3 |
| InvA | 4.4 | 6.0 | 52.2 | 68.8 | 12.0 | 8.7 | −1.3 |
| InvB | 24.0 | 52.7 | 65.3 | 77.4 | 2.7 | −0.8 | −1.2 |
| InvC | 3.3 | 11.0 | 45.7 | 65.6 | 14.0 | 4.2 | −1.4 |
| InvE | 1.1 | 0.7 | 2.6 | 3.2 | 2.4 | 3.9 | −1.2 |
| InvF | 0.5 | 1.5 | 5.2 | 2.2 | 9.6 | 3.5 | 2.4 |
| InvG | 10.2 | 20.7 | 30.0 | 46.2 | 3.0 | 1.5 | −1.5 |
| InvH | 9.8 | 10.0 | 20.9 | 21.5 | 2.1 | 2.1 | −1.0 |
| InvJ | 3.6 | 32.7 | 1.3 | 18.3 | −2.8 | −25.0 | −14.0 |
| OrgA | 2.9 | 6.7 | 18.3 | 21.5 | 6.3 | 2.7 | −1.2 |
| OrgB | 13.1 | 13.0 | 57.4 | 25.8 | 4.4 | 4.4 | 2.2 |
| PrgH | 19.3 | 26.3 | 97.9 | 108.6 | 5.1 | 3.7 | −1.1 |
| PrgI | 0.5 | 0.5 | 0.7 | 10.8 | 1.2 | 1.3 | −16.5 |
| PrgJ | 0.5 | 0.5 | 2.6 | 4.3 | 4.8 | 5.2 | −1.6 |
| PrgK | 18.5 | 17.3 | 113.5 | 86.0 | 6.0 | 6.6 | 1.3 |
| SicA | 29.1 | 53.3 | 57.4 | 92.5 | 2.0 | −0.9 | −1.6 |
| SicP | 0.5 | 3.7 | 7.8 | 14.0 | 14.4 | 2.1 | −1.8 |
| SigE | 18.2 | 23.3 | 41.8 | 57.0 | 2.3 | 1.8 | −1.4 |
| SipA | 29.4 | 165.3 | 61.3 | 220.4 | 2.1 | −2.7 | −3.6 |
| SipB | 109.7 | 253.3 | 693.0 | 478.4 | 6.3 | 2.7 | 1.4 |
| SipC | 83.9 | 150.7 | 390.2 | 250.5 | 4.6 | 2.6 | 1.6 |
| SipD | 10.9 | 71.3 | 67.9 | 103.2 | 6.2 | −1.1 | −1.5 |
| SlrP | 0.9 | 6.3 | 2.6 | 33.3 | 2.9 | −2.4 | −12.8 |
| SopA | 8.0 | 23.3 | 47.0 | 91.4 | 5.9 | 2.0 | −1.9 |
| SopB | 70.9 | 152.7 | 197.1 | 369.8 | 2.8 | −0.8 | −1.9 |

TABLE 6-continued

Spectral counts obtained by LC-MS/MS analysis of T3SS-associated proteins in minicell and rod samples from ΔminD S. typhimurium overexpressing the T3SS positive transcription regulator HilA.

| | Spectral Counts | | | | Relative Abundance (Fold Difference)[1] | | |
|---|---|---|---|---|---|---|---|
| Protein | Minicells | Rods | Minicells (+HilA) | Rods (+HilA) | Minicells (+HilA) versus minicells | Minicells (+HilA) versus rods | Minicells (+HilA) versus rods (+HilA) |
| SopD | 0.5 | 4.3 | 23.5 | 64.5 | 43.1 | 5.4 | −2.7 |
| SopE | 18.9 | 18.7 | 63.9 | 51.6 | 3.4 | 3.4 | 1.2 |
| SopE2 | 0.5 | 3.7 | 7.8 | 22.6 | 14.4 | 2.1 | −2.9 |
| SpaO | 10.5 | 14.7 | 35.2 | 29.0 | 3.3 | 2.4 | 1.2 |
| SpaP | 0.9 | 1.7 | 28.7 | 6.5 | 31.6 | 17.2 | 4.5 |
| SpaS | 5.1 | 4.0 | 2.6 | 5.4 | −1.9 | −1.5 | −2.1 |
| SptP | 2.5 | 30.3 | 5.2 | 179.5 | 2.1 | 0.2 | −34.4 |

[1]Relative abundance was determined by comparing the average spectral counts of rod and minicell samples Minicells Assemble Functional Type III Secretion Systems A functional SPI-1 T3SS machine must be able to deploy the protein translocases SipB, SipC, and SipD, which will eventually mediate the passage of the secreted proteins through the mammalian cell membrane (Collazo and Galán, 1997, Mol. Microbiol. 24:747-756). Prior to contact with host cells, only SipD, a component of the needle tip complex, is displayed on the bacterial surface (Lara-Tejero and Galan, 2009, Infect Immun 77:2635-2642). To probe for the presence of potentially functional T3SS complexes, minicells were examined by immunofluorescence microscopy for the presence of surface-localized SipD. It was found that a significant proportion of minicells isolated from bacterial cells overexpressing HilA displayed SipD on their surface (FIG. 2A and FIG. 2B). In contrast, minicells isolated from a SPI-1 T3SS-defective mutant did not (FIG. 2A and FIG. 2B). These results indicate that minicells assemble T3SS complexes potentially competent for protein translocation into mammalian cells.

Minicells are metabolically active and capable of synthesizing de novo plasmid-encoded proteins after the partitioning of plasmids into minicells (Frazer and Curtiss, 1975, Curr Top Microbiol Immunol. 69:1-84). It was therefore investigated whether purified minicells were competent for the secretion and translocation into cultured mammalian cells of a de novo synthesized SPI-1 T3SS effector protein. Minicells were isolated from T3SS-competent or T3SS-defective strains carrying a plasmid which encodes the effector protein SopB (Galyov et al., 1997, Mol Microbiol 25:1903-1912) expressed from an arabinose-inducible promoter. Isolated minicells were incubated in the presence of arabinose for 3 hours and the secretion of SopB to culture medium was assessed by Western immunoblot analysis. SopB was detectable in supernatants of T3SS-competent minicells but not from supernatants of T3SS-defective minicells despite equivalent amount of SopB in lysates of whole minicells obtained from either strain (FIG. 2C and FIG. 7B). One of the characteristic features of some T3SSs such as the one encoded by the S. typhimurium SPI-1 is that their activity is stimulated upon contact with eukaryotic cells (Zierler and Galan, 1995, InvJ. Infect Immun 63:4024-4028). Consistent with this behavior, greater levels of secreted SopB was observed upon exposure of minicells to cultured Henle-407 epithelial cells (FIG. 2D). The ability of minicells to inject proteins to cultured epithelial cells was also examined using a fractionation protocol previously developed to detect translocated effector proteins in the cytosol of infected cells (Collazo and Galán, 1997, Mol. Microbiol. 24:747-756). Detectable levels of translocated SopB was found in preparation of cultured cells exposed to minicells obtained from wild-type S. typhimurium but not in those exposed to minicells obtained from a SPI-1 T3SS-defective mutant (FIG. 2E). These results indicate that minicells assemble a functional T3SS capable of mediating protein secretion and translocation into eukaryotic cells.

T3SS in Minicells can Deliver Antigen In-vitro

It has been previously shown that live, virulence-attenuated S. typhimurium can deliver heterologous antigens in a T3SS-dependent manner to the major class I antigen presentation pathway (Russmann et al., 1998, Science 281:565-568). To determine whether the T3SS in minicells was also capable of such delivery, the first 104 amino acids of SopE, containing the T3SS-targeting signal (Evans et al., 2003, J. Virol. 77:2400-2409), were fused to 16 amino acids of the OVA antigen containing the class I restricted SIINFEKL peptide (SEQ ID NO: 1) (Dick et al., 1994, Journal of Immunology 152:3884-3894) along with a C-terminal 3×FLAG tag (SopE-OVA) (FIG. 3A). A plasmid encoding this chimeric protein was introduced into minicell-producing T3SS-competent or T3SS-defective S. typhimurium strains (FIG. 3B and FIG. 7C). The ability of minicells to deliver SopE-OVA in a T3SS-dependent manner to the class I antigen-presenting pathway was then tested. Murine RMA cells were incubated with minicells purified from different parental strains and the ability of the RMA cells to present the class I restricted OVA peptide to the class I-restricted B3Z T-cell reporter (Karttunen et al., 1992, Proc Natl Acad Sci USA. 89:6020-6024) was assayed by measuring β-galactosidase production by the reporter cells. Minicells purified from T3SS-competent S. typhimurium were found to efficiently deliver SopE-OVA to RMA cells (FIG. 3C). In contrast, minicells obtained from a T3SS-defective mutant were not (FIG. 3C). These results demonstrate that minicells are capable of T3SS-dependent translocation of an effector-antigen construct. In addition, these results indicate that minicell T3SS-delivered effector-antigen constructs can elicit a MHC class I restricted immune response and activation of $CD8^+$ T-cells in vitro.

Although purified minicells were shown to be capable of delivering antigen in a T3SS-dependent manner, the efficiency of delivery was relatively poor. While not be wishing to be bound by any particular theory, this inefficiency might be at least partially due to the lower levels of some critical components of the T3SS in minicells. Secretion of proteins through the T3SS requires customized cytoplasmic chaperones, which target them to the secretion machinery (Galan and Wolf-Watz, 2006, Nature 444:567-573). Since proteomic analysis indicated that the partitioning of the SopE chaperone InvB (as well as other T3SS chaperones) into minicells was inefficient (Table 5), invB was added to the plasmid expressing the chimeric sopE-OVA construct that partitions into minicells. Expression of invB in tandem with sopE-OVA improved the relative antigen presentation of minicells by over 2-fold (FIG. 3C). The proteomics analysis also showed that the translocases SipB, SipC, and SipD and their associated chaperones InvE and SicA were also depleted in minicells (Table 5). Consequently, the genes encoding these proteins were added to the expression plasmid. Although expression of the antigen construct was slightly lower (FIG. 3B and FIG. 7C), minicells obtained from this strain showed a significantly higher antigen presenting ability, achieving a level essentially equivalent to that of the peptide positive control (FIG. 3C). These results show that the T3SS-mediated antigen delivery by purified minicells can be optimized by the expression of T3SS components encoded by plasmids that can partition into minicells.

Dendritic cell (DC) immunotherapy is emerging as a promising strategy for autologous treatment of infectious diseases and cancer (Tacken, et al., 2007, Nat Rev Immunol. 7:790-802). Some configurations of this strategy involve the ex vivo antigen loading of autologous DCs prior to their application back to the recipients. Minicells could potentially offer advantages for ex vivo loading of DCs since not only they can deliver antigen to the class I antigen presenting pathway, essential in anti-tumor immune responses, but also they can potentially deliver DC maturation signals through the Toll-receptor agonists present in these nanoparticles. It was therefore tested whether minicells could deliver antigen to DCs ex vivo. Mouse bone marrow-derived DCs were incubated with minicells obtained from strains carrying a plasmid expressing sopE-OVA along with its chaperone invB and the protein translocases and their chaperones (FIG. 3D and FIG. 7D). Antigen loading was assayed by measuring the ability of dendritic cells to present the class I restricted OVA peptide to the class I-restricted allogeneic B3Z T-cell reporter cell. It was found that the response elicited by the minicell-pulsed DCs in the reporter cell line was equivalent to the peptide positive control (FIG. 3E). Antigen presentation was strictly dependent on the presence of the T3SS in the minicells since DCs pulsed with equivalent number of minicells obtained from a T3SS-deficient bacterial strain did not elicit a response in the reporter cell line (FIG. 3D, FIG. 3E, and FIG. 7D). These results show that minicells can effectively deliver antigen to DCs ex vivo.

T3SS in Minicells can Prime $CD8^+$ T-cell Responses In Vivo

The potential of minicells expressing SopE-OVA to prime $CD8^+$ T-cell responses in vivo was evaluated. OT-I $CD8^+$ T-cells (CD45.2), which can specifically recognize an OVA epitope (Hogquist et al., 1994, Cell 76:17-27), were adoptively transferred into C57BL/6J congenic mice expressing CD45.1. Recipient mice were then immunized with purified minicells optimized for the delivery of SopE-OVA by co-expressing the chaperone InvB and the translocases. As controls, mice were immunized with minicells obtained from a T3SS-defective strain expressing SopE-OVA or minicells obtained from a T3SS-competent strain that did not express SopE-OVA (FIG. 4A and FIG. 7E). After three weeks, the recipient mice were boosted with recombinant VSV-OVA and 5 days after the boost mice were sacrificed and the expansion of OT-I $CD8^+$ T-cells was analyzed. Mice immunized with minicells purified from the wild-type parental vaccine strain expressing SopE-OVA had a significant expansion of the CD45.2 $CD8^+$ donor OT-I T-cells specific for the OVA peptide (FIG. 4B). In contrast, mice immunized with minicells expressing SopE-OVA purified from a T3SS-defective background or minicells lacking SopE-OVA, did not show expansion of the adoptively transferred OT-I $CD8^+$ T-cells upon boosting with VSV-OVA (FIG. 4B). These results indicate that minicells can prime antigen-specific $CD8^+$ T-cell responses in vivo in a T3 SS-dependent manner.

The ability of minicells to elicit a protective immune response in a mouse model of *Listeria monocytogenes* infection was also evaluated. Ex vivo bone-marrow derived dendritic cells were stimulated with minicells expressing a chimera consisting of the secretion and translocation domain of SopE fused to *Listeria monocytogenes* MHC class I restricted immunogenic peptides from listeriolysin O and p60 (SopE-Lis) (FIG. 4C), which have been shown to induce protective $CD8^+$ T-cell responses in Balb/c mice (Harty and Bevan, 1992, J. Exp. Med. 175:1531-1538; Harty and Pamer, 1995, J. Immunol. 154:4642-4650). For controls, dendritic cells were stimulated ex vivo with purified minicells obtained from a T3SS-defective strain expressing SopE-Lis or minicells obtained from a T3SS-competent strain that did not express SopE-Lis (FIG. 4D and FIG. 7F). Stimulated dendritic cells were then transferred by tail vein injection into recipient mice, and 6 days after the transfer, recipient mice were challenged with *L. monocytogenes*. Three days after challenge, mice were sacrificed and the c. f. u. of *Listeria monocytogenes* in the spleens were enumerated. significantly lower number of c. f. u. were found in the spleens of mice that had received dendritic cells stimulated with T3SS-competent minicells expressing the *L. monocytogenes* antigens compared to control animals (FIG. 4E). These results demonstrate that dendritic cells stimulated ex vivo by T3SS-competent minicells can confer protection from an infectious challenge.

Antigen Delivery System

The present studies described herein demonstrate a strategy to engineer the *S. typhimurium* T3SS into nanoparticles capable of delivering antigens directly into the cytosol of antigen presenting cells to stimulate the production of protective, antigen-specific class I-restricted $CD8^+$ T-cells. The development of these nanoparticles expands the potential of the T3SS as an antigen delivery system of heterologous antigens by providing a safer, non-replicating vehicle for vaccination against infections in which this type of response is crucial for protection. In addition, this system may provide an effective strategy to prime dendritic cells ex vivo for immunotherapy against infectious diseases and cancer.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of delivering a compound of interest into a recipient cell comprising contacting the recipient cell with the compound of interest, wherein the compound of interest was secreted by a bacterial minicell, thereby delivering the compound of interest to the recipient cell, wherein the bacterial minicell is an achromosomal nanoparticle, and wherein the bacterial minicell comprises a functional type III secretion system (T3SS) and the compound of interest.

2. The method of claim 1, wherein the bacterial minicell is derived from bacteria, wherein the bacteria comprises an isolated nucleic acid comprising an nucleic acid sequence encoding HilA.

3. The method of claim 2, wherein the bacteria comprises a mutant form of at least one selected from the group consisting of minA, minB, minC, minD, ftsA, ftsZ, and zipA, thereby rendering the bacteria replication deficient.

4. The method of claim 1, wherein the bacterial minicell is modified to increase the expression of at least one selected from the group consisting of a T3SS component and a T3SS regulator.

5. The method of claim 1, wherein the bacterial minicell comprises at least one isolated nucleic acid comprising a nucleic acid sequence encoding at least one of the group consisting of HilA, InvB, SipB, SipC, SipD, InvE, SicA, and SigE.

6. The method of claim 1, wherein the compound of interest is an antigen.

7. The method of claim 1, wherein the recipient cell is an antigen presenting cell.

8. The method of claim 1, wherein the compound of interest is selected from the group consisting of a peptide, a protein, a nucleic acid, and a small molecule.

9. The method of claim 1, wherein the bacterial minicell and recipient cell are in an environment selected from in vivo, ex vivo, or in vitro.

* * * * *